US006770622B2

(12) United States Patent
Jarvis et al.

(10) Patent No.: US 6,770,622 B2
(45) Date of Patent: Aug. 3, 2004

(54) N-TERMINALLY TRUNCATED GALECTIN-3 FOR USE IN TREATING CANCER

(76) Inventors: Gary A. Jarvis, VA Medical Center, 4150 Clement St., San Francisco, CA (US) 94121; Constance M. John, VA Medical Center, 4150 Clement St., San Francisco, CA (US) 94121; Hakon Leffler, Institute of Laboratory Medicine, Lund University, Solvegatan 23, SE-223 62 Lund (SE)

( * ) Notice: Subject to any disclaimer, the term of this patent is extended or adjusted under 35 U.S.C. 154(b) by 0 days.

(21) Appl. No.: 09/877,790

(22) Filed: Jun. 8, 2001

(65) Prior Publication Data

US 2003/0054982 A1 Mar. 20, 2003

(51) Int. Cl.$^7$ .......................... A61K 38/00; A61K 38/16; C07K 17/00
(52) U.S. Cl. ................................ 514/8; 514/2; 530/350
(58) Field of Search .......................... 514/2, 8; 530/350

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,439,196 A | 3/1984 | Higuchi |
| 4,447,224 A | 5/1984 | DeCant, Jr. et al. |
| 4,447,233 A | 5/1984 | Mayfield |
| 4,475,196 A | 10/1984 | La Zor |
| 4,486,194 A | 12/1984 | Ferrara |
| 4,487,603 A | 12/1984 | Harris |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands et al. |
| 4,925,678 A | 5/1990 | Ranney |
| 4,959,217 A | 9/1990 | Sanders et al. |
| 5,011,771 A | 4/1991 | Bellet et al. |
| 5,167,616 A | 12/1992 | Haak et al. |
| 5,169,383 A | 12/1992 | Gyory et al. |
| 5,192,659 A | 3/1993 | Simons |
| 5,225,182 A | 7/1993 | Sharma |
| 5,272,057 A | 12/1993 | Smulson et al. |
| 5,281,521 A | 1/1994 | Trojanowski et al. |
| 5,681,923 A | 10/1997 | Platt |
| 5,801,002 A | 9/1998 | Raz |
| 5,837,493 A | 11/1998 | Hillman et al. |
| 5,895,784 A | 4/1999 | Raz et al. |

FOREIGN PATENT DOCUMENTS

WO    WO98/22139    5/1998

OTHER PUBLICATIONS

Yang et al (Biochemistry 1998; 37:4086–4092).*
Woo HJ et al (J. Biol Chem 1990;265(13):7097–7099).*
Akahani, S., P. Nangia–Makker, H. Inohara, H.R. Kim, and A. Raz. 1997. Galectin–3: a novel antiapoptotic molecule with a functional BH1 (NWGR) domain of Bcl–2 family. Cancer Res. 57:5272–5276.
Andre, S., S. Kojima, N. Yamazaki, C. Fink, H. Kaltner, K. Kayser, and H.J. Gabius. 1999. Galectins–1 and –3 and their ligands in tumor biology. Non–uniform properties in cell-surface presentation and modulation of adhesion to matrix glycoproteins for various tumor cell lines, in biodistribution of free and liposome–bound galectins and in their expression by breast and colorectal carcinomas with/without metastatic propensity. J Cancer Res Clin Oncol.125:461–474.
Barondes, S.H., D.N. Cooper, M.A. Gitt, and H. Leffler. 1994. Galectins. Structure and function of a large family of animal lectins. J Biol Chem. 269:20807–20810.
Barondes, S.H., V. Castronovo, D.N. Cooper, R.D. Cummings, K. Drickamer, T. Feizi, M.A. Gitt, J. Hirabayashi, C. Hughes, K. Kasai, and et al. 1994. Galectins: a family of animal beta–galactoside–binding lectins[letter]. Cell. 76:597–598.
Bresalier, R.S., N. Mazurek, L.R. Sternberg, J.C. Byrd, C.K. Yunker, P. Nangia–Makker, and A. Raz. 1998. Metastasis of human colon cancer is altered by modifying expression of the beta–galactoside–binding protein galectin 3. Gastroenterology. 115:287–296.
Castronovo, V., F.A. Van Den Brule, P. Jackers, N. Clausse, F.T. Liu, C. Gillet, and M.E. Sobel. 1996. Decreased expression of galectin–3 is associated with progression of human breast cancer. J Pathol. 179:43–48.
Gaudin, J.C., B. Mehul, and R.C. Hughes. 2000. Nuclear localisation of wild type and mutant galectin–3 in transfected cells. Biol Cell. 92:49–58.
Glinsky, V.V., M.E. Huflejt, G.V. Glinsky, S.L. Deutscher, and T.P. Quinn. 2000. Effects of Thomsen–Friedenreich antigen–specific peptide P–30 on beta–galactoside–mediated homotypic aggregation and adhesion to the endothelium of MDA–MB–435 human breast carcinoma cells. Cancer Res. 60:2584–2588.

(List continued on next page.)

Primary Examiner—Gary Nickol
Assistant Examiner—Christopher Yaen
(74) Attorney, Agent, or Firm—Kohn & Associates, PLLC; Kenneth I. Kohn; Amy E. Rinaldo

(57) ABSTRACT

There is provided a composition having an effective amount of N-terminally truncated galectin-3 in a pharmaceutically acceptable carrier. Also provided by the present invention is a method of treating cancer by administering to a patient in need of such treatment an effective amount of N-terminally truncated galectin-3 in a pharmaceutically acceptable carrier.

2 Claims, 15 Drawing Sheets

OTHER PUBLICATIONS

Gong, H.C., Y. Honjo, P. Nangia–Makker, V. Hogan, N. Mazurak, R.S. Bresalier, and A. Raz. 1999. The NH2 terminus of galectin–3 governs cellular compartmentalization and functions in cancer cells. *Cancer Res.* 59:6239–6245.

Hsu, D.K., R.I. Suberi, and F.T. Liu. 1992. Biochemical and biophysical characterization of human recombinant IgE–binding protein, an S–type animal lectin. *J. Biol. Chem.* 267:14167–14174.

Idikio, H. 1998. Galectin–3 expression in human breast carcinoma: correlation with cancer histologic grade. *Int J Oncol.* 12:1287–1290.

Inohara, H., and A. Raz. 1995. Functional evidence that cell surface galectin–3 mediates homotypic cell adhesion. *Cancer Res.* 55:3267–3271.

Itzkowitz, S.H. 1997. Galectins: multipurpose carbohydrate–binding proteins implicated in tumor biology. *Gastroenterology.* 113:2003–2005.

Kaltner, H., K.S. Lips, R.G. Lippert, F. Sinowatz, and H.J. Gabius. 1997. Quantitation and histochemical localization of galectin–1 and galectin–1–reactive glycoconjugates in fetal development of bovine organs. *Histol Histopathol.* 12:945–960.

Kim, H.R., H.M. Lin, H. Biliran, and A. Raz. 1999. Cell cycle arrest and inhibition of anoikis by galectin–3 in human breast epithelial cells. *Cancer Res.* 59:4148–4154.

Kuwabara, I., and F.T. Liu. 1996. Galectin–3 promotes adhesion of human neutrophils to laminin. *J Immunol.* 156:3939–3944.

Le Marer, N., and R.C. Hughes. 1996. Effects of the carbohydrate–binding protein galectin–3 on the invasiveness of human breast carcinoma cells. *J Cell Physiol.* 168:51–58.

Leffler, H. 1997. Introduction to galectins. *Trends Glycosci Glycotechnol.* 45:9–19.

Leffler, H., and S.H. Barondes. 1986. Specificity of binding of three soluble rat lung lectins to substituted and unsubstituted mammalian beta–galactosides. *J Biol Chem.* 261:10119–10126.

Lindstedt, R. 1993. Lectins at Epithelial Surfaces. In Department of Medical Microbiology. University of Lund, Lund, Sweden.

Lindstedt, T., G. Apodaca, S.H. Barondes, K. Mostov, and H. Leffler. 1993. Apical secretion nof a cytosolic protein by Madin–Darby canine kidney cells. Evidence for polarized release of an endogenous lectin by a nonclassical secretary pathway. *J Biol Chem.* 268:11750–11757.

Liu, F.T., D.K. Hsu, R.I. Zuberi, P.N. Hill, A. Shenhav, I. Kuwabara, and S.S. Chen. 1996. Modulation of functional properties of galectin–3 by monoclonal antibodies binding to the non–lectin domains. *Biochemistry.* 35:6073–6079.

Lotz, M.M., C.W. Andrews, Jr., C.A. Korzelius, E.C. Lee, G.D. Steele, Jr., A. Clarke, and A.M. Mercurio. 1993. Decreased expression of Mac–2 (carbohydrate binding protein 35) and loss of its nuclear localization are associated with the neoplastic progression of colon carcinoma. *Proc Natl Acad Sci U S A.* 90:3466–3470.

Martin, A.N., J. Swarbrick, and A. Cammarata. 1996. Physical Pharmacy. Lea & Febiger, Philadelphia.

Massa, S.M., D.N. Cooper, H. Leffler, and S.H. Barondes. 1993. L–29, an endogenous lectin, binds to glycoconjugate ligands with positive cooperativity. *Biochemistry.* 32:260–267.

Matarrese, P., N. Tinari, J. Semeraro, C. Natoli, S. Iacobelli, and W. Malorni. 2000. Galectin–3 overepression protects from cell damage and death by influencing mitochrondrial homeostatis. *FEBS letters.* 473:311–315.

Matarrese, P., O. Fusco, N. Tinari, C. Natoli, F.T. Liu, M.L. Semeraro, W. Malorni, and S. Iacobelli. 2000. Galectin–3 overexpression protects from apoptosis by improving cell adhesion properties. *Int J Cancer.* 85:545–554.

Mehul, B., S. Bawumia S.R. Martin, and R.C. Hughes. 1994. Structure of baby hamster kidney carbohydrate–binding protein CBP30, an S–type animal lectin. *J Biol Chem.* 269:18250–18258.

Menon, R.P., and R.C. Hughes. 1999. Determinants in the N–terminal domains of galectin–3 for secretion by a novel pathway circumventing the endoplasmic reticulum–Golgi complex. *Eur J Biochem.* 264:569–576.

Nangia–Makker, P., R. Sarvis, D.W. Visscher, J. Bailey–Penrod, A. Raz, and F.H. Sarkar. 1998. Galectin–3 and L1 retrotransposons in human breast carcinomas. *Breast Cancer Res Treat.* 49:171–183.

Nangia–Makker, P., Y. Honjo, R. Sarvis, S. Akahani, V. Hogan, K.J. Pienta, and A. Raz. 2000. Galectin–3 induces endothelial cell morphogenesis and angiogenesis. *Am J Pathol.* 156:899–909.

Ochieng, J., D. Platt, L. Tait, V. Hogan, T. Raz. P. Carmi, and A. Raz. 1993. Structure–function relationship of a recombinant human galactoside–binding protein. *Biochemistry.* 32:4455–4460.

Ochieng, J., M.L. Leite–Browning, and P. Warfield. 1998. Regulation of cellular adhesion to extracellular matrix proteins by galectin–3. *Biochem Biophys Res Commun.* 246:788–791.

Ochieng, J., P. Warfield, B. Green–Jarvis, and I. Fentie. 1999. Galectin–3 regulates the adhesive interaction between breast carcinoma cells and elastin. *J Cell Biochem.* 75:505–514.

Oda, Y., H. Leffler, Y. Sakakura, K. Kasai, and S.H. Barondes. 1991. Human breast carcinoma cDNA encoding a galactoside–binding lectin homologous to mouse Mac–2 antigen. *Gene.* 99:279–283.

Perillo, N.L., M.E. Marcus, and L.G. Baum. 1998. Galectins: versatile modulators of cell adhesion, cell proliferation, and cell death. *Journal of Molecular Medicine.* 76:402–412.

Pienta, K.J., H. Naik, A. Akhtar, K. Yamazaki, T.S. Replogle, J. Lehr, T.L. Donat, L. Tait, V. Hogan, and A. Raz. 1995. Inhibition of spontaneous metastasis in a rat prostate cancer model by oral administration of modified citrus pectin [see comments]. *J Natl Cancer Inst.* 87:348–353.

Prochiantz, A. 2000. Messenger proteins: homeoproteins, TAT and others. *Curr Opin Cell Biol.* 12:400–406.

Rabinovich, G.A. 1999. Galectins: an evolutionarily conserved family of animal lectins with multifunctional properties; a trip from the gene to clinical therapy. *Cell Death Differ.* 6:711–721.

Rabinovich, G.A., C.M. Riera, C.A. Landa, and C.E. Sotomayor. 1999. Galectins: a key intersection between glycobiology and immunology. *Braz J Med Biol Res.* 32:383–393.

Raz, A., and R. Lotan. 1981. Lectin–like activities associated with human and murine neoplastic cells. *Cancer Res.* 41:3642–3647.

Raz, A., D.G. Zhu, V. Hogan, N. Shah, T. Raz, R. Karkash, G. Pazerini, P. Carmi. 1990. Evidence for the role of 34–kDa galactoside–binding lectin in transformation and metastasis. *Int J Cancer.* 46:871–877.

Raz, A., G. Pazerini, and P. Carmi. 1989. Identification of the metastasis–associated, galactoside–binding lectin as a chimeric gene product with homology to an IgE–binding protein. *Cancer Res*. 49:3489–3493.

Rowland, M., and T.N. Tozer. 1995. Clinical Pharmacokinetics. Williams & Wilkins, Baltimore.

Sano, H., D.K. Hsu, L. Yu, J.R. Apgar, I. Kuwabara, T. Yamanaka, M. Hirashima, and F.T. Liu. 2000. Human galectin–3 is a novel chemoattractant for monocytes and macrophages. *J Immunol*. 165:2156–2164.

Seetharaman, J., A. Kanigsberg, R. Slaaby, H. Leffler, S.H. Barondes, and J.M. Rini. 1998. X–ray crystal structure of the human galectin–3 carbohydrate recognition domain at 2.1–A resolution. *J Biol Chem*. 273:13047–13052.

Sparrow, C.P., H. Leffler, and S.H. Barondes. 1987. Multiple soluble beta–galactoside–binding lectins from human lung. *J Biol Chem*. 262:7383–7390.

Wang, L., H. Inohara, K.J. Pienta, and A. Raz. 1995. Galectin–3 is a nuclear matrix protein which binds RNA. *Biochem Biophys Res Commun*. 217:292–303.

Yamaoka, A., I. Kuwabara, L.G. Frigeri, and F.T. Liu. 1995. A human lectin, galectin–3 (epsilon bp/Mac–2), stimulates superoxide production by neutrophils. *J Immunol*. 154:3479–3487.

Yang, M., E. Baranov, P. Jiang, F.–X. Sun, X.–M. Li, S. Hasegawa, M. Bouvet, M. Al–Tuwaijri, T. Chishima, H. Shimada, A. Moossa, S. Penman, and R. Hoffman. 2000. Whole–body optical imaging of green fluorescent protein-expressing tumors and metastases. *Proc Natl Acad Sci USA*. 97:1206–1211.

Yang, R.–Y., D. Hsu, and F.–T. Liu. 1996. Expression of galectin–3 modulates T–cell growth and apoptosis. *Proc Natl Acad Sci USA*. 93:6737–6742.

Zar, J.H. 1996. Biostatistical Analysis. Prentice–Hall, Englewood Cliffs, N.J.

* cited by examiner

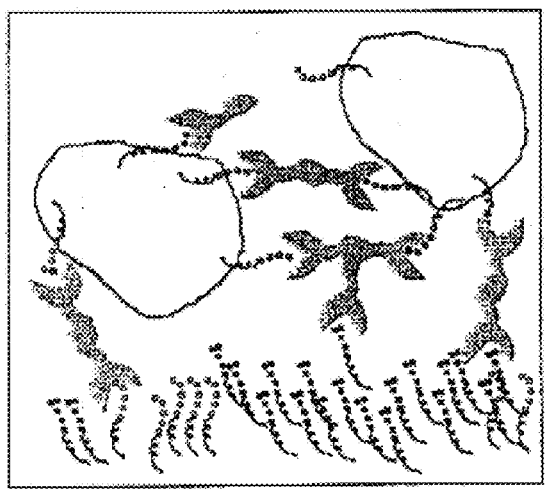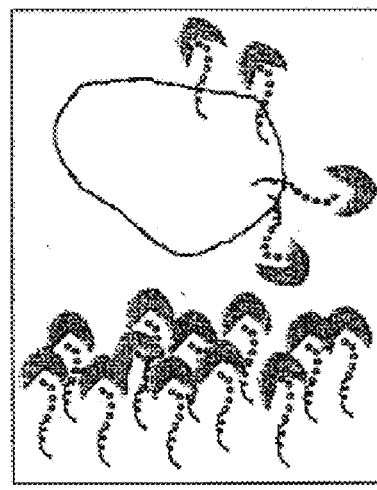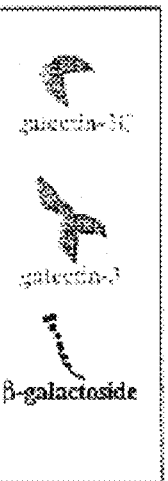
FIG. 1A  FIG. 1B

FIG. 9A (Control group)
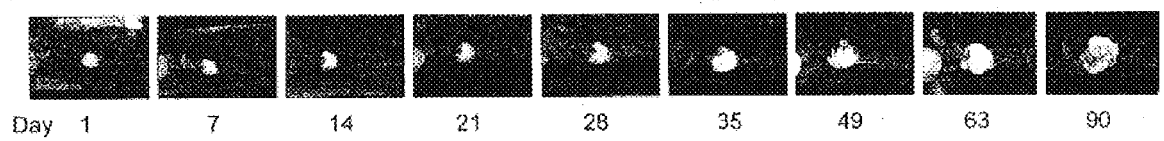
Day 1   7   14   21   28   35   49   63   90
FIG. 9B (Galectin-3 treated group)
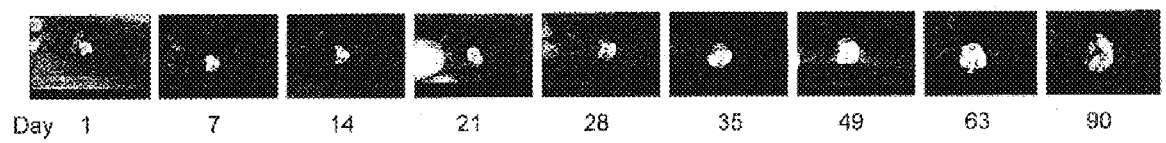
Day 1   7   14   21   28   35   49   63   90
FIG. 9C (Galectin-3C treated group)
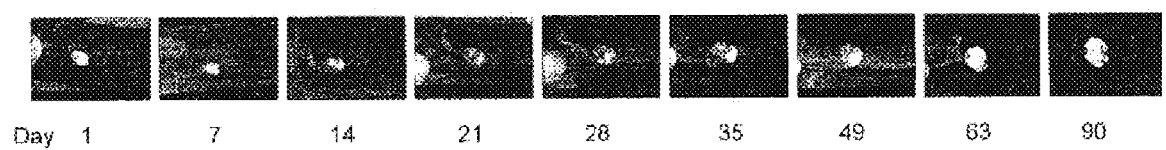
Day 1   7   14   21   28   35   49   63   90
Typical representative has been chosen for each group Primary tumor Lymph node metastasis Lung metastasis Liver Metastasis Primary tumor Lymph node metastasis Lung metastasis Liver Metastasis

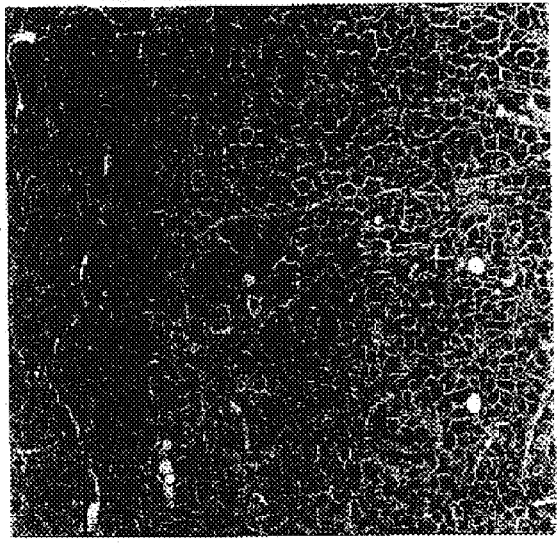
FIG. 12A Primary tumor
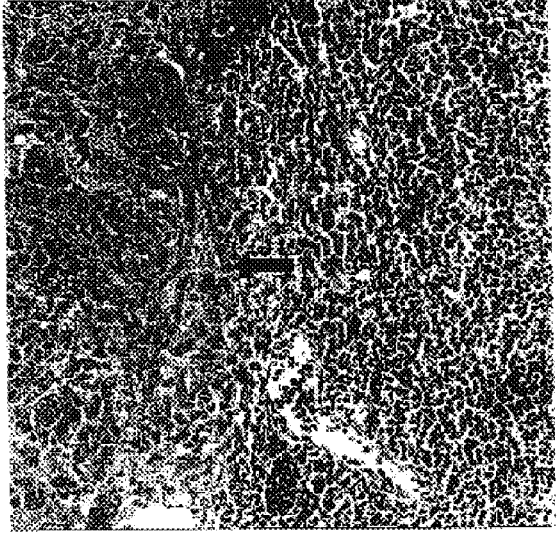
FIG. 12B Lymph node metastasis
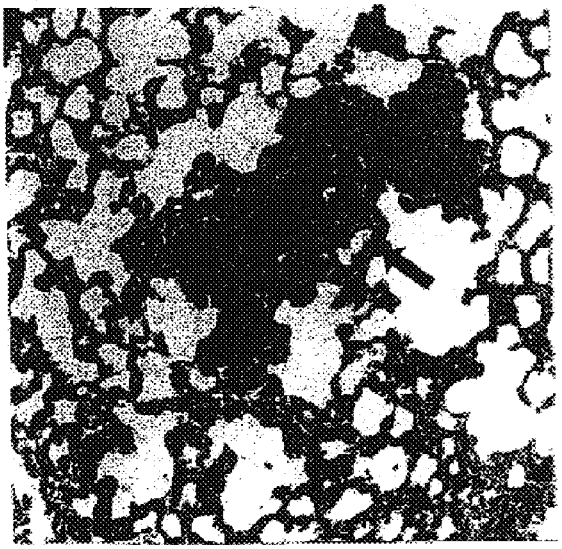
FIG. 12C Lung metastasis

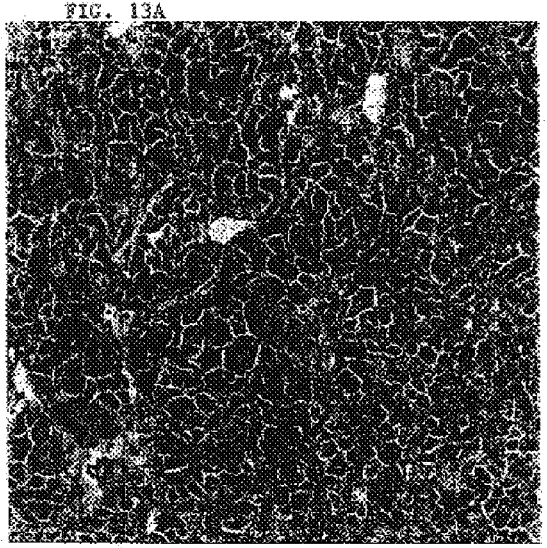
Primary tumor
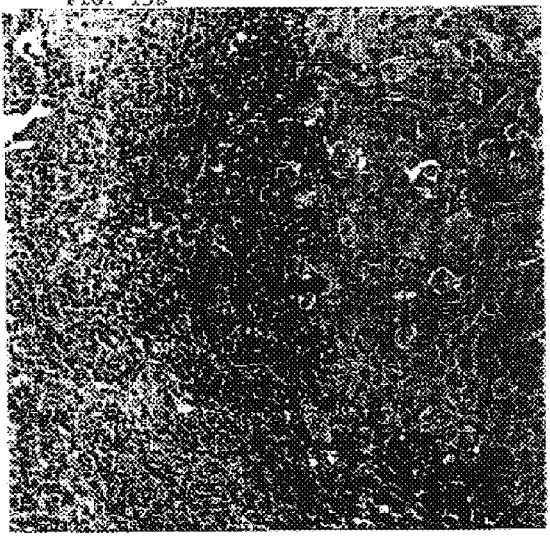
Lymph node metastasis
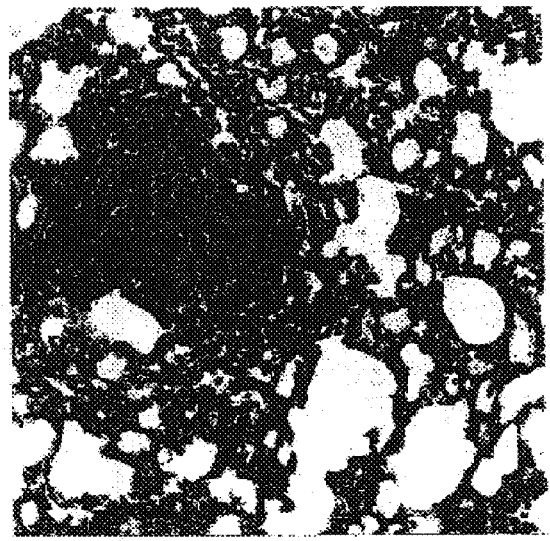
Lung metastasis
FIG. 13C Primary tumor Lymph node metastasis Lung metastasis

N-TERMINALLY TRUNCATED GALECTIN-3 FOR USE IN TREATING CANCER

BACKGROUND OF THE INVENTION

1. Technical Field

The present invention relates to methods and compositions for treating cancer.

2. Background Art

There is evidence that tumor cell metastasis is, in part, due to complex intercellular interactions involving adhesion and aggregation. A specific class of tumor proteins, lectins, that play a role in cell adhesion are now known to be important in tumor formation and metastasis.

Lectins are, by definition, proteins with at least one carbohydrate-binding domain. By immobilizing monosaccharides, oligosaccharides, or glycoproteins in affinity columns, lectins have been isolated from tumor tissue extracts. Generally, a tissue extract in acetone or the like is prepared to isolate the protein component from the lipid component. The acetone is then evaporated, whereupon the residue is solublized in a buffered aqueous solution. This solution is then passed through an affinity column containing the immobilized carbohydrates or glycoproteins. A number of lectins, which selectively bind to galactosides, have been isolated in this manner.

Galectin-3 is one member of the family of lectins termed galectins, formerly known as S-type or S-Lac lectins. Galectins-are classified as such due to structural similarity and characteristic affinity for β-galactoside sugars (1, 2). The highest levels of galectin-3 are found in activated macrophages, basophils, mast cells, some epithelial cells, and sensory neurons. An early observation was that many tumor cells express galectins on their surface and that their expression could be involved in adhesion and invasion processes. Experimental evidence also suggested that these galectins could be cross-linked by an exogenous glycoprotein resulting in the aggregation of tumor cells. Based on these results, Raz and Lotan proposed that galectin-1 and galectin-3 could promote tumor metastasis (3). Since that time, the evidence for the role of galectin-3 in tumor adhesion, invasion and metastasis has mounted.

Galectin-3 is composed of three distinct structural motifs: a short amino terminal region of 12 amino acids, a sequence rich in G-X-Y tandem repeats characteristic of the collagen supergene family, and a carboxy-terminal half containing the globular carbohydrate recognition domain (2, 4–6). There is close homology between the galectin-3 proteins of different species, but the number of N-terminal tandem repeats differs, hence, the sizes of the proteins vary (7). The human protein is composed of 250 amino acid residues with a $M_r$ of ~31,000 (5) and a carbohydrate recognition domain extending from 117 to 250. The X-ray crystal structure of the human galectin-3 carbohydrate recognition domain complexed with lactose and N-acetyllactosamine has been published (8).

Although all galectins bind lactose with similar affinity, each galectin is more specific and has higher affinity for certain more complex saccharides (9, 10). Galectins, in general, are unusual among extracellular proteins in that they are initially mainly cytosolic but can be secreted by non-classical pathways, translocated to the cell nucleus, and endocytosed and trancytosed by cells. Galectins are thought to interact with various cell-surface and extracellular glycoproteins and glycolipids, thereby playing a role in cell adhesion, migration, and signaling. The relationship between the intra- and extracellular functions of galectins may be of great biological importance. A number of reviews of the biology of the galectins have been published (11–15).

Galectin-3 can be found on the plasma membrane, and depending on the cell type can be both the nuclear and cytoplasmic or limited to the cytoplasm (6, 16–18). Galectin-3 can be secreted and reuptaken into cells by a nonclassical mechanism (19–21). Studies of mutants of hamster galectin-3 with various deletions in the N-terminal domain have shown that the even if lacking the first 103 amino acid residues the protein is localized in the nucleus. Deletion of the first 110 amino acid residues, however, prevented nuclear localization, although the exact sequence of amino acid residues 104–110, APTGALT, was not obligatory and substitution of other unrelated sequences permitted nuclear sequestration (18). The amino acid residues 104–110 of the hamster galectin-3 protein according to the consensus sequence correspond to the amino acid residues 109–115 of the homologous human galectin-3 protein (7).

Galectin-3 shares the ability to be secreted despite the absence of a signal peptide with a number of other proteins that have unconventional intercellular transfer. These proteins are internalized by cells and are able to directly access the cytoplasm and the nucleus by a process that does not involve classical endocytosis (22). This is in contrast with the modulation of intercellular events by second messengers that bind to extracellular receptors and initiate a cascade of intracellular events that often involve transcriptional regulation. Although the mechanisms for the ability of some proteins to cross biological membranes in the absence of a signal sequence are poorly understood, a number of common features have been identified. Many of the proteins can directly access the nucleus, their mechanisms for secretion often vary from their mechanisms for entry, and apolipoproteins and cholesterol can play a role (22).

Galectin-3 is isolated as a monomer but undergoes multimerization on binding to surfaces that contain glycoconjugate ligands, and the N-terminal half of the protein is required for this property (23, 24). The N-terminal domain of the protein is required for galectin-3 to have affinity for multivalent carbohydrate ligands (23, 25) and to transmit intracellular signals (6, 26). Galectin-3 promotes binding of cells to laminin and fibronectin, but the N-terminally truncated protein does not (27). Thus, the N-terminal domain appears to be necessary for the self-association of galectin-3 that are required for some of its biological functions. Galectin-3 null cells were transfected to express recombinant galectin-3 and induced tumors within 4 weeks when injected into mice. When the same galectin-3 null cells were transfected to express a mutant galectin-3 that was lacking the 11 amino terminal amino acids no tumors developed within 4 weeks (6).

A number of laboratories have studied the biology of galectin-3 that apparently is significant in cell growth, differentiation, adhesion, RNA processing, apoptosis, and malignant transformation (28). Laminin is the major noncollagenous polypeptide of basement membranes, and galectin-3 binds preferentially to mouse tumor laminin compared to human placental laminin (29). Galectin-3 has been shown to increase the binding of breast cancer cells to other extracellular matrix proteins (29, 30). In addition to increasing the binding of tumor cells to basement membranes, the interaction of cell surface galectin-3 with complementary serum glycoproteins appears to promote aggregation of tumor cells in circulation, thereby playing another important role in the pathogenesis of metastasis (31).

Expression of recombinant galectin-3 in weakly metastatic fibrosarcoma cells resulted in an increased incidence of experimental lung metastases in syngeneic and nude mice (32). In human umbilical vein endothelial cells (HUVEC) galectin-3 induces angiogenesis (33). Increased expression of galectin-3 in human colon cancer cells resulted in increased metastases, and reduction in galectin-3 expression from antisense DNA was associated with decreased liver colonization and spontaneous metastasis in athymic nude mice (34). Exogenous galectin-3 has been shown to increase invasiveness of human breast cancer cells (35), and to be a chemotactic factor for human umbilical vein endothelial cells (34). However, the endogenous expression of galectin-3 by the cells was not correlated with their invasiveness (35). Introduction of human galectin-3 cDNA into the human breast cancer cells BT-549 which are galectin-3 null and non-tumorigenic in nude mice resulted in the establishment of four galectin-3 expressing clones, three of which acquired tumorigenicity when injected into nude mice (36). Nonetheless, the role of galectin-3 in cancer is complicated, and a number of different laboratories have found that decreased expression of galectin-3 is associated with increased tumorigenicity and metastasis (16, 37–39). Overall, the body of work regarding the biochemistry and function of galectin-3 provides a strong rationale for continued exploration of its therapeutic use in cancer.

Galectin-3 is not a member of the Bcl-2 family of proteins, but at residues 180–183 it contains the four amino acid motif (NWGR) conserved in the BH1 domain of the Bcl-2 family, and it has 48% sequence similarity with Bcl-2 (40). Galectin-3 has antiapoptotic activity that is abrogated by substitution of the Gly182 residue with Ala in the NWGR motif (41, 42). In T cells galectin-3 interacts with Bcl-2 in a lactose inhibitable manner and confers resistance to apoptosis induced by anti-Fas antibody and staurosporine (40). Galectin-3 has been found to improve cellular adhesion and prevent apoptosis induced by loss of cell anchorage (anoikis) (42–44). Contact with the extracellular matrix is required for suppression of apoptosis of epithelial cells from a number of tissues.

By providing a mechanism for adherence of tumor cells to one another and to the extracellular matrix (27) and the subsequent suppression of apoptotis, galectin-3 on the surface of tumor cells appears to contribute to tumor invasion and metastasis. This premise is supported by the inhibition of spontaneous metastasis in a rat prostate cancer model by oral administration of modified citrus pectin, a complex polysaccharide rich in galactosyl residues. Citrus pectin (pH modified), a plant fiber component, can directly bind galectin-3, and can interfere with carbohydrate-mediated cell-cell and cell-matrix interactions (45).

U.S. Pat. No. 5, 681,923, to Platt (1997), discloses the active site of galactose binding proteins. Two different peptide sequences are claimed that correspond to part of galectin-3 are claimed. One peptide is composed of 25 amino acids corresponding to residues 171 to 196 of galectin-3. The second peptide is 38 amino acids and corresponds to residues 158 to 196 of galectin-3. In both peptides there is a histidine instead of aspartic acid 178 of galectin-3. The X-ray crystal structure of the human galectin-3 carbohydrate recognition domain in complex with lactose and N-acetyllactosamine has been published (8). The carbohydrate recognition domain of galectin-3 extends from amino acid 117 to 250 with some of the residues between 144 and 184 directly involved in hydrogen binding to lactosaminylated substrates (8). It would instead be useful to develop a larger peptide region for use in treating cancer. A larger fragment would be likely to be more effective than the peptides that were disclosed in the Platt patent.

U.S. Pat. No. 5,801,002, to Raz (1998), discloses sequences for the human galectin-3 protein. However, there is not disclosure regarding use of inhibition of the multimerization of galectin-3 that is required for many of the biological functions of the protein in cellular adhesion and signaling as a treatment. The N-terminal domain of the protein is critical for the multimerization of galectin-3 when it is bound to carbohydrate ligands. Thus, it could be useful to develop a fragment of galectin-3 having a deleted the N-terminal region so that it would still have the carbohydrate recognition domain and would still be able to bind to carbohydrate ligands for use in treating patients. This is because the N-terminally truncated galectin-3 does not have the ability to cross-link cells with other cells and to extracellular matrix. U.S. Pat. No. 5,801,002 describes using peptides as therapeutic agents that correspond to at least 4 consecutive amino acid residues of galectin-3. However, in U.S. Pat. No. 5,801,002 there is no indication that one or another of these would be better or worse in inhibition of metastasis.

U.S. Pat. 5,895,784, to Raz et al. (1999), discloses the use of pH-modified citrus pectin to treat cancer. Additionally, the Raz et al. patent describes the function, structure and expression of galectin-3. The inventors indicate that they used citrus pectin to study the properties of galectin-3 and claim a method of treating cancer by oral administration of modified pectin that can bind to the carbohydrate domain of galectin-3 to reduce metastasis. There is no disclosure of a truncated form of galectin-3 that prevents tumorigenicity and metastasis.

PCT WO 98/122139 (PCT/US97/21807), to Huflejt et al. (1998), discloses the detection of human galectin-4 in various samples. Although the focus is on galectin-4, some of the methods described include the use of galectin-3 as controls. Again, there is no disclosure of a truncated form of galectin-3 that prevents tumorigenicity and metastasis is not disclosed nor described.

U.S. Pat. No. 5, 837,493, to Hillman et al. (1998), discloses some descriptions of galectin-1, -2, and -3 including descriptions of the lectin structures and amino acid sequences. The sequence and the prevention of disease by two novel human galectins are disclosed. However, there is no disclosure of a truncated form of galectin-3 that prevents tumorigenicity and metastasis is not disclosed nor described.

The regulatory mechanism that produces the variable localization of galectin-3 in different cell types is not understood, and the significance of the relative amounts of the protein found in the cytoplasm, or nucleus, or extracellular matrix of various cell types in terms of functionality is not understood. Many laboratories have studied the role of galectin-3 in cancer, and although the results of the studies are somewhat confusing they do indicate that galectin-3 is of significance in some types of cancer. However, the prior art is lacking in a methodology and a composition of galectin-3 that can be successfully used to treat cancer. It would therefore be useful to develop a method and a composition based on an N-terminally truncated form of galectin-3 that can be used successfully to reduce tumor growth and metastasis.

SUMMARY OF THE INVENTION

According to the present invention, there is provided a composition having an effective amount of an N-terminally truncated galectin-3 that is lacking the N-terminal 107 amino acids in a pharmaceutically acceptable carrier. Also provided by the present invention is a method of treating a cancer in a patient by administering to a patient in need of such treatment an effective amount of N-terminally truncated galectin-3 in a pharmaceutically acceptable carrier.

DESCRIPTION OF THE DRAWINGS

Other advantages of the present invention are readily appreciated, as the same becomes better understood by reference to the following detailed description when considered in connection with the accompanying drawings wherein:

FIG. 1 is a schematic showing a postulated mechanism of action of N-terminally truncated galectin-3 whereby the truncated form of the protein inhibits the binding of intact galectin-3 to carbohydrate ligands and thereby also inhibits the multimerization and cross-linking activities of galectin-3.

FIG. 9 is a series of photographs showing the efficacy evaluation of N-terminally truncated galectin-3 against the GFP-Gene Transfected Human Breast Cancer MDA-MB435 in a mouse model;

FIGS. 12 A–C are photographs showing a representative histopathology of primary tumor and lymph node, and lung metastasis in mice treated with N-terminally truncated galectin-3;

FIGS. 13 A–C are photographs showing a representative histopathology of primary tumor, lymph node, and lung metastasis in mice treated with N-terminally truncated galectin-3;

DETAILED DESCRIPTION OF THE INVENTION

Figure 2:
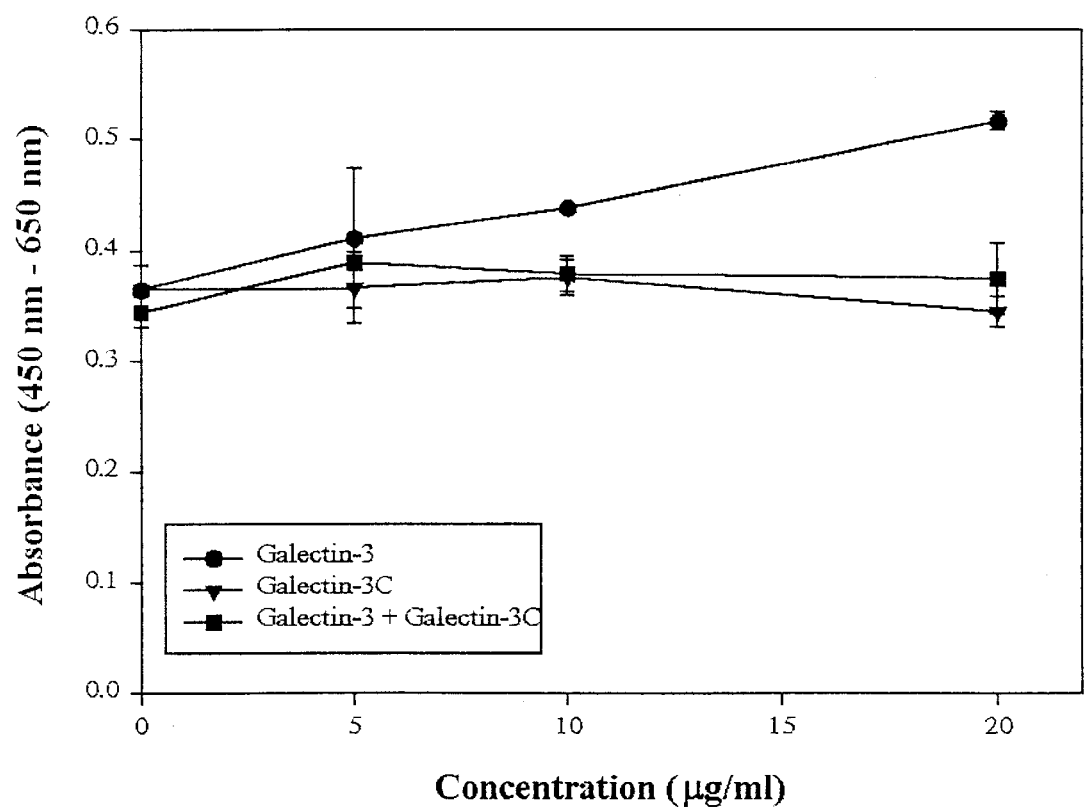
FIG. 2 is a graph showing the absorbance at 450 nm due to the active metabolism of WST-1 by cells that have bound to laminin in the presence of galectin-3, N-terminally truncated galectin-3 (galectin-3C), or a mixture of both galectin-3 and the N-terminally truncated galectin-3.

The present invention provides a method and composition for treating cancer by administering an effective amount of N-terminally truncated galectin-3 placed in an acceptable pharmaceutically carrier.

In accordance with the present invention, there is provided an N-terminally truncated galectin-3 lacking the N-terminal 107 amino acids that was produced by enzymatic cleavage of the recombinant protein followed by collection of the pharmacologically active fragment, in the preferred method. Alternative methods can also be used as are known to those of skill in the art. Also, there are provided N-terminally truncated human galectin-3 molecules that differ slightly in length being somewhat longer or shorter than the N-terminally truncated galectin-3 lacking the N-terminal 107 amino acids that have essentially the same ability to inhibit the carbohydrate binding and multimerization of galectin-3 and, therefore, inhibit tumorigenicity and metastatsis in vivo. The methods to produce these slightly different versions of the N-terminally truncated human galectin-3 protein are known to those of skill in the art. The steps in the preferred method include first producing intact recombinant human galectin-3 was produced in *Escherichia coli* Bl21(DE3) transfomed with pET3cGal3 (the pET3c plasmid containing the human galectin-3 coding DNA) as described previously (23). Next, the bacteria were lysed by sonication and the galectin-3 protein purified by affinity chromatography on lactosyl-Sepharose (23) then dialyzed to remove lactose. The product was then cleaved with *Clostridium perfringens* collagenase type VII (Sigma Chemical Co., St. Louis, Mo.). Specifically, the recombinant galectin-3 was incubated overnight at 37° C. with a lectin:collagenase ratio of 20:1 (by weight) in 20 mM Tris-HCl, pH 7.4, 150 mM. NaCl, and 1 mM $CaCl_2$. The resulting N-terminally truncated galectin-3 was purified by affinity chromatography on lactosyl-Sepharose. For storage and shipment a procedure was used involving dialysis against water followed by lyophilization. The dry N-terminally truncated galectin-3 powder was stored at −20° C. for various amounts of time, up to three months. The retention of the carbohydrate binding activity of an aliquot was ascertained by testing on a small lactosyl-Sepharose column. This established that N-terminally truncated galectin-3 can be stored and shipped as a lyophilized powder without losing activity.

The amino acid sequence of the N-terminally truncated recombinant human galectin-3 that is produced by exhaustive digestion with collagenase, and that is designated as SEQ ID NO. 1, is as follows:

gap agplivpynl plpggvvprm litilgtvkp nanrialdfq rgndvafhfn prfnennrrv ivcntkldnn wgreerqsvf pfesgkpfki qvlvepdhfk vavndahllq ynhrvkklne isklgisgdi ditsasytmi The amino acid sequence of the intact recombinant human galectin-3 described by Oda et al. (46) is designated herein as SEQ ID NO. 2, and its sequence is as follows:

1 madnfslhda lsgsgnpnpq gwpgawgnqp agaggypgas ypgaypgqap pgaypgqapp 61 gayhgapgay pgapapgvyp gppsgpgayp ssgqpsapga ypatgpygap agplivpynl 121 plpggvvprm litilgtvkp nanrialdfq rgndvafhfn prfnennrrv ivcntkldnn 181 wgreerqsvf pfesgkpfki qvlvepdhfk vavndahllq
ynhrvkklne isklgisgdi 241 dltsasytmi Alternate cloning methods also can be used to produce the N-terminally truncated galectin-3 that lacks the N-terminal 107 amino acids. For example, a plasmid containing the complete galectin-3 coding sequence is used as a template in a PCR reaction using primers designed to amplify the desired fragment. The forward primer is (5'-GACGACGACAAGggcgccctgctgggccactg-3') and reverse primer is (5'-GAGGAGAAGCCCGGTgccccttcagattatatc-3'). The noncapitalized sequences are part of the gene sequence for the galectin-3 protein. The noncapitalized sequence of the forward primer corresponds to the sequence of the N-terminally truncated galectin-3 protein that starts at amino acid 108 corresponding to Gly. The noncapitalized sequence of the reverse primer corresponds to the polyA tail of the gene on the C-terminal end. The capitalized sequences are added as tails and used to fuse the PCR product with pET32 Ek/LIC plasmid using the Ek/LIC ligation protocol (Novagen). This plasmid produces a fusion protein with a variety of unique binding qualities and endoprotease sites allowing for high yields and purity of the recombinant protein. $E.coli$ BL21(DE3) is transformed with this construct and used for protein production. Expression of the galectin-3 protein is under the control of bacteriophage T7 promoter and transcription is initiated by providing a source of T7. RNA polymerase (such as infection with a phage that carries the T7. RNA polymerase gene or moving the plasmid into a cell containing an expression host containing a copy of the T7. RNA polymerase gene).

The present invention provides the use of the C-terminal domain of galectin-3 as a therapeutic agent. The N-terminal domain is not required for oligosaccharide binding, but is required for positive cooperativity (23). The result of the positive cooperativity is multimers of galectin-3 binding to the substrate surface (23). Thus, galectin-3 multimers could cross-link a tumor cell with the extracellular membrane. The C-terminal fragment competitively inhibits the binding of galectin-3 to substrates.

More specifically, soluble recombinant N-terminally truncated galectin-3 effectively competes with endogenous galectin-3 for carbohydrate binding sites in the extracellular matrix and cell-cell adhesions important in tumor invasion and metastasis. The N-terminal domain of galectin-3 promotes multimerization of the protein, and enables it to cross link cancer cells to the matrix and other cells. Excess administered N-terminally truncated galectin-3, in which the N-terminal part of the protein has been removed, occupies binding sites of endogenous galectin-3 and prevents its cross-linking activities. N-terminally truncated galectin-3 itself does not have significant cross-linking activity since it lacks the N-terminal part of galectin-3, and acts like a dominant-negative inhibitor of galectin-3.

Recombinant N-terminally truncated galectin-3 is efficacious for inhibition of tumor invasion and metastasis in cancer. The mechanism shown in FIG. 1 is the competitive inhibition by recombinant galectin-3 of the binding of the galectin-3 on the surface of metastatic cancer cells to laminin and other β-galalctoside glycoconjugates in the extracellular matrix. The N-terminal domain of galectin-3 promotes its multimerization and, thus, enables it to cross link cancer cells to the matrix and to other cells. Excess administered truncated galectin-3, in which the N-terminal part of the galectin-3 has been removed, occupies the galectin-3 carbohydrate binding sites in the extracellular matrix and in cell-cell adhesions important in tumor invasion and metastasis. This truncated version of galectin-3 itself should has cross-linking activity since it lacks the N-terminal domain of galectin-3. Hence, N-terminally truncated galectin-3 acts like a dominant-negative inhibitor of galectin-3 and prevent galectin-3 mediated binding of cells to the extracellular matrix and cell-cell adhesion as shown in FIG. 1. This concept is supported by the fact that galectin-3 itself, but not the N-terminally truncated galectin-3 produced by collagenase digestion, promotes binding of cells to laminin and fibronectin (27). Thus, the N-terminally truncated galectin-3 molecule by blocking the multimerization of the intact protein prevents the adhesion of tumor cells with one another and with the extracellular matrix. In addition to preventing adhesion to the extracellular matrix and, thus, metastasis, prevention of the contact of cancer cells with the extracellular matrix can also lead to their programmed cell death or apoptosis that is induced by loss of cell anchorage (also called anoikis) (42, 43).

The amount of N-terminally truncated galectin-3, which is utilized in the composition of the present invention, is a sufficient amount to at least reduce tumor size. Alternatively, it can prevent or reduce metastasis of a tumor. The tumors being treated can include breast cancer, prostate cancer, colon cancer, lung cancer, and all additional solid and liquid forms of cancer.

Alternatively, the compound of the present invention can be useful in preventing tumor growth. In such an example, by maintaining the N-terminally truncated galectin-3 titers in the body of an individual, the composition can prevent tumor growth by preventing tumors from forming in the first place. As stated in the Background Art, it is known that lectins could be useful in treating tumors and preventing metastasis, accordingly, by creating a preventative treatment that prevents the long term growth of tumor cells in the body, the compound of the present invention can be useful in preventing initial tumor growth. The amount of composition for treatment is based upon the body weight of the individual being treated. This can be determined by individuals of skill in the art.

In order to effectuate the treatment of the present invention, there is administered to a patient an effective amount of the N-terminally truncated galectin-3 in a pharmaceutically acceptable carrier. Administration can occur intramuscularly, orally, intravenously, locally, subcutaneously or in any other mechanism known to those of skill in the art. The mechanism of treatment varies depending upon the cancer that is being treated and can be best determined by those of skill in the art.

Figure 3:
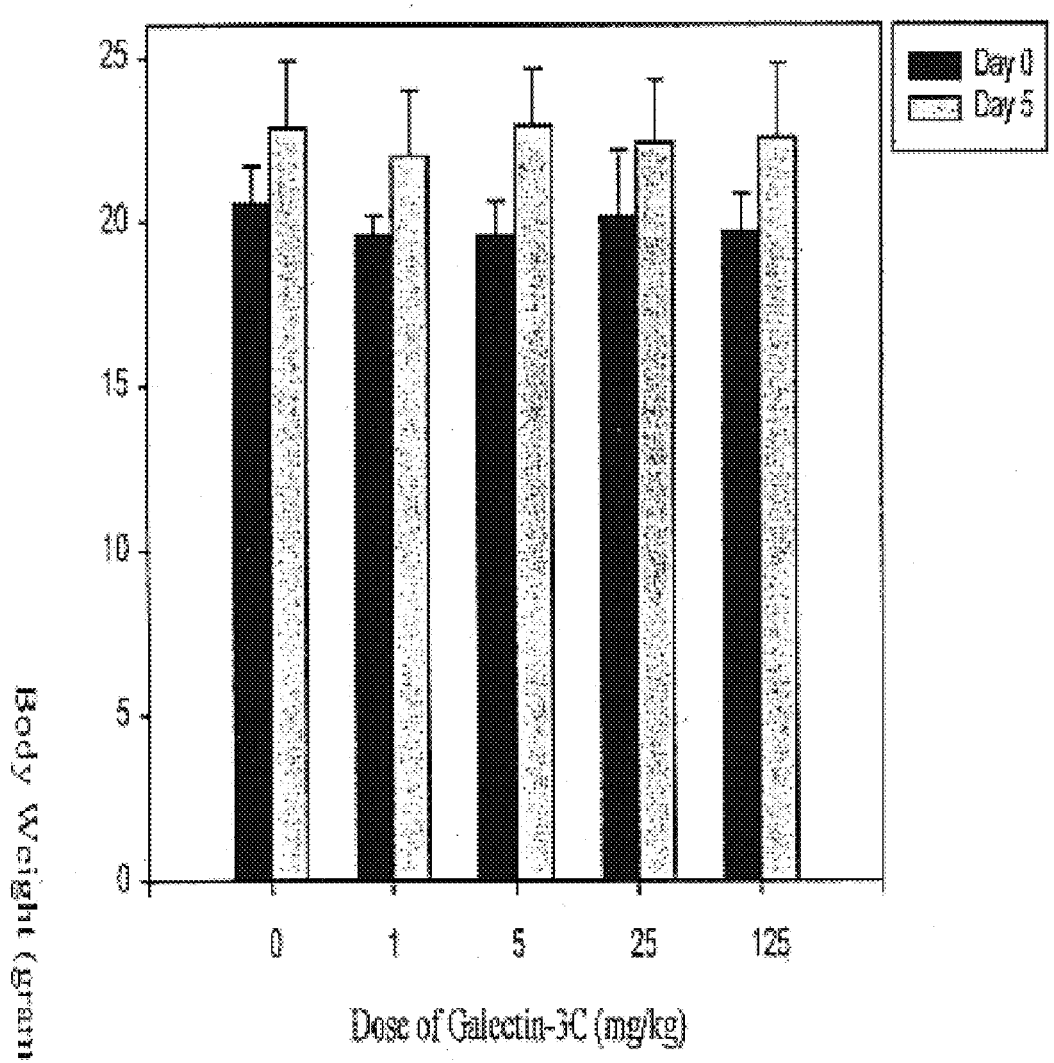
FIG. 3 is a graph showing the maximum tolerated dose determination based on the body weight versus a dose of N-terminally truncated galectin-3.

For example, N-terminally truncated galectin-3 was evaluated as a potential therapeutic agent for breast cancer based on the lectin galectin-3. It was determined that therapy with an N-terminally truncated form of galectin-3 is efficacious for inhibition of metastases. To this end, recombinant galectin-3 was produced and the N-terminally truncated galectin-3 was derived by collagenase enzyme digestion and affinity chromatography. Injected N-terminally truncated galectin-3 was detected by metabolic labeling with $^{35}S$ methionine prior to collagenase cleavage. As shown in FIG. 3 the maximum tolerated dose of N-terminally truncated galectin-3 in nude mice was determined to be greater than 125 mg/kg without overt adverse effects. The pharmacokinetic elimination half-life of N-terminally truncated galectin-3 administered intramuscularly into nude mice was found to be 4.56 hours. Mice bearing orthotopically implanted tumors derived from breast cancer cell line MDA-MB435 were treated intramuscularly twice daily for 90 days with N-terminally truncated galectin-3 or a vehicle control. It was found that the mean tumor volumes and weights were statistically significantly less in mice treated with N-terminally truncated galectin-3 compared with control mice, and that fewer numbers of mice exhibited lymph node metastases in the treated group compared with the control group. It was therefore concluded that N-terminally truncated galectin-3 is not overtly toxic and is efficacious in reducing metastases and tumor volumes and weights in primary tumors.

Additionally, the compound of the present invention can be utilized in a combination therapy. This can include adding to the pharmaceutically acceptable carrier additional chemotherapeutic compounds for further treatment of the cancer cells.

The above discussion provides a factual basis for the use of the compositions of the present invention. The method used with and the utility of the present invention can be shown by the following non-limiting examples and accompanying figures.

EXAMPLES

General methods in molecular biology: Standard molecular biology techniques known in the art and not specifically described were generally followed as in Sambrook et al., *Molecular Cloning: A Laboratory Manual*, Cold Spring Harbor Laboratory Press, New York (1989), and in Ausubel et al., *Current Protocols in Molecular Biology*, John Wiley and Sons, Baltimore, Md. (1989) and in Perbal, *A Practical Guide to Molecular Cloning*, John Wiley & Sons, New York (1988), and in Watson et al., Recombinant DNA, Scientific American Books, New York and in Birren et al (eds) *Genome Analysis: A Laboratory Manual Series*, Vols. 1–4. Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in *PCR Protocols: A Guide To Methods And Applications*, Academic Press, San Diego, Calif. (1990). In-situ (In-cell) PCR in combination with Flow Cytometry can be used for detection of cells containing specific DNA and mRNA sequences (Testoni et al, 1996, Blood 87:3822.)

General methods in immunology: Standard methods in immunology known in the art and not specifically described are generally followed as in Stites et al.(eds), Basic and Clinical Immunology (8th Edition), Appleton & Lange, Norwalk, Conn. (1994) and Mishell and Shiigi (eds), Selected Methods in Cellular Immunology, W.H. Freeman and Co., New York (1980).

Immunoassays

In general, ELISAs are the preferred immunoassays employed to assess a specimen. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, *Molecular Cloning: A Laboratory Manual*, Cold Springs Harbor, N.Y., 1989.

Antibody Production

Antibody Production: Antibodies can be either monoclonal, polyclonal or recombinant. Conveniently, the antibodies can be prepared against the immunogen or portion thereof for example a synthetic peptide based on the sequence, or prepared recombinantly by cloning techniques or the natural gene product and/or portions thereof can be isolated and used as the immunogen. Immunogens can be used to produce antibodies by standard antibody production technology well known to those skilled in the art as described generally in Harlow and Lane, *Antibodies: A Laboratory Manual*, Cold Spring Harbor Laboratory, Cold Spring Harbor, N.Y., 1988 and Borrebaeck, *Antibody Engineering—A Practical Guide*, W.H. Freeman and Co., 1992. Antibody fragments can also be prepared from the antibodies and include Fab, F(ab')$_2$, and Fv by methods known to those skilled in the art.

For producing polyclonal antibodies a host, such as a rabbit or goat, is immunized with the immunogen or immunogen fragment, generally with an adjuvant and, if necessary, coupled to a carrier; antibodies to the immunogen are collected from the sera. Further, the polyclonal antibody can be absorbed such that it is monospecific. That is, the sera can be absorbed against related immunogens so that no cross-reactive antibodies remain in the sera rendering it monospecific.

For producing monoclonal antibodies the technique involves hyperimmunization of an appropriate donor with the immunogen, generally a mouse, and isolation of spleenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

For producing recombinant antibody (see generally Huston et al, 1991; Johnson and Bird, 1991; Mernaugh and Mernaugh, 1995), messenger RNAs from antibody producing B-lymphocytes of animals, or hybridoma are reverse-transcribed to obtain complimentary DNAs (cDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

The antibody can be bound to a solid support substrate or conjugated with a detectable moiety or be both bound and conjugated as is well known in the art. (For a general discussion of conjugation of fluorescent or enzymatic moieties see Johnstone & Thorpe, *Immunochemistry in Practice*, Blackwell Scientific Publications, Oxford, 1982.) The binding of antibodies to a solid support substrate is also well known in the art. (see for a general discussion Harlow & Lane *Antibodies: A Laboratory Manual*, Cold Spring Harbor Laboratory Publications, New York, 1988 and Borrebaeck, *Antibody Engineering—A Practical Guide*, W.H. Freeman and Co., 1992) The detectable moieties contemplated with the present invention can include, but are not limited to, fluorescent, metallic, enzymatic and radioactive markers such as biotin, gold, ferritin, alkaline phosphatase, b-galactosidase, peroxidase, urease, fluorescein, rhodamine, tritium, $^{14}C$. and iodination.

Delivery of Gene Products/Therapeutics (Compound):

The compound of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound or as pharmaceutically acceptable salt and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

It is noted that humans are treated generally longer than the mice or other experimental animals exemplified herein which treatment has a length proportional to the length of the disease process and drug effectiveness. The doses can be single doses or multiple doses over a period of several days, but single doses are preferred.

The doses can be single doses or multiple doses over a period of several days. The treatment generally has a length proportional to the length of the disease process and drug effectiveness and the patient species being treated.

When administering the compound of the present invention parenterally, it is generally formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, can also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it is desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the compound utilized in the present invention can be administered orally to the patient. Conventional methods such as administering the compounds in tablets, suspensions, solutions, emulsions, capsules, powders, syrups and the like are usable. Known techniques which deliver it orally or intravenously and retain the biological activity are preferred.

In one embodiment, the compound of the present invention can be administered initially by intravenous injection to bring blood levels to a suitable level. The patient's levels are then maintained by an oral dosage form, although other forms of administration, dependent upon the patient's condition and as indicated above, can be used. The quantity to be administered varies for the patient being treated and varies from about 100 ng/kg of body weight to 100 mg/kg of body weight per day and preferably is from 10 mg/kg to 10 mg/kg per day.

Example 1

As background for the following example, mounting evidence suggests that tumor cells express the β-galactoside-binding lectin galectin-3 on their surfaces and that tumor cells metastasize partly due to processes involving cellular adhesion and aggregation mediated by galectin-3. Galectin-3 binds via its C-terminus carbohydrate recognition domain to binding sites in the extracellular matrix (1). The goal of this research was the evaluation of a potential therapeutic agent for breast cancer based on galectin-3 lectin that acts directly to reduce metastases. Soluble recombinant N-terminally truncated galectin-3 competes with endogenous galectin-3 for carbohydrate binding sites in the extracellular matrix and cell-cell adhesions important in tumor invasion and metastasis. The N-terminal domain of galectin-3 promotes multimerization of the protein, and enables it to cross link cancer cells to the matrix and other cells (31). Excess administered N-terminally truncated galectin-3, in which the N-terminal part of the protein has been removed, occupies binding sites of endogenous galectin-3 and prevents its cross-linking activities. N-terminally truncated galectin-3 itself has less cross-linking activity since it lacks the N-terminal part of galectin-3, and acts like a dominant-negative inhibitor of galectin-3, as shown in FIG. 1. The experiments establish that therapy with recombinant N-terminally truncated galectin-3 is efficacious for inhibition of tumor invasion and metastasis in breast cancer. The overall purpose was to determine the efficacy, safety and mechanism of action of N-terminally truncated galectin-3 in treatment of metastatic breast cancer using a nude mouse model of metastasis.

Preparation for Animal Studies

The carbohydrate recognition domain of galectin-3 (N-terminally truncated galectin-3) was produced as described previously (23). High yield expression (20–300 mg/liter culture) of active soluble galectin-3 can be obtained. The intact recombinant galectin-3 was produced in *Escherichia coli* B121/DE3 containing the pET3c plasmid (Novagen) with the human galectin-3 coding DNA (pET3cGal3). Galectin encoding DNA can be amplified by PCR using galectin cDNA as template and primers that contain restriction sites for cloning of the product into the expression vector in the proper reading frame. The PCR product is first cloned into the TA-vector (Invitrogen, Carlsbad, Calif.), the insert released with the restriction enzymes corresponding to the primers and finally cloned into the expression vector. The expression construct is used to transform the proper host strain (e.g. *E. coli* BL21 for the pET system). The organisms were lysed by sonication and the galectin-3 protein purified by affinity chromatography on lactosyl-Sepharose (23). The purified galectin-3 was dialyzed to remove lactose and cleaved with *Clostridium perfringens* collagenase type VII (Sigma). The resulting N-terminally truncated galectin-3 was purified again by affinity chromatography on lactosyl-Sepharose.

For storage and shipment a new procedure was developed involving dialysis against water followed by lyophilization. The dry N-terminally truncated galectin-3 powder was stored at −20° C. for various amounts of time up to three months and the retention of the carbohydrate binding activity of an aliquot was ascertained by testing on a small lactosyl-Sepharose column. Other batches (with or without enrichment in $^{15}N$) were analyzed by NMR-spectroscopy. This analysis confirmed that the protein had retained its proper folding. Therefore, N-terminally truncated galectin-3 can be stored and shipped as a lyophilized powder without loosing activity.

To produce $^{35}S$ labeled N-terminally truncated galectin-3 for pharmacokinetic studies, the plasmid pET3cGal3 was transfected into *E. coli* B834 (Novagen), which is a methionine auxiotroph derived from BL21/DE3. The *E. coli* were adapted for growth on M9 minimal medium supplemented with ampicillin (50 mg/ml) and methionine (40 mg/ml)(M9-Met) by passage on M9-Met plates three times. To produce $^{35}S$ galectin-3, a colony from the last plate was inoculated into 0.5 liters of M9-Met supplemented with 1.0 mCi $^{35}S$-Met. The bacteria were cultured, induced with IPTG and harvested as described previously (23). To lyse the radioactive *E. Coli*, sonication was avoided because of aerosol formation. Various alternative methods were tested and the following method was determined to be most efficient. To the bacterial pellet there was added 5 ml sucrose (25%) in 50 mM TrisHCl, pH 8.0 with 50 mM NaCl, 20 mM EDTA, and 8 mg lysozyme. After ten minutes on ice, 16 ml water was added and the sample kept on ice another 30 minutes. The sample was centrifuged at 12000 rpm for 30 minutes and the supernatant applied to lactosyl-Sepharose. The galectin-3 was eluted, dialyzed and treated with collagenase to generate N-terminally truncated galectin-3 as described above.

Cellular Adhesion Assay

A cellular adhesion assay was performed similar to that described previously (27) in 96-well microtiter plates. The wells were coated with 50 microliters of 20 micrograms/ml of human laminin in PBS overnight at 4° C. The wells then were washed once with minimum essential media (MEM), and then blocked for 1 hour at 37° C. with 1% R.I.A. grade BSA in MEM, washed once with MEM containing 0.1% Tween-20 and twice with MEM. To each well was added $4.5 \times 10^4$ human breast cancer cells, MDA-MB435 with various concentrations of galectin-3, the N-terminally truncated galectin-3, or a mixture of both proteins. Either 0, 5, 10, 15, or 20 micrograms per ml of galectin-3 or the N-terminally truncated protein were added in MEM. In a third set of wells, 20 micrograms per ml of N-terminally truncated galectin-3 was added with 5, 10, 15, or 20 micrograms per ml of galectin-3 in MEM. After incubation for 15 minutes at 37° C. the nonadherent cells were removed and the wells gently washed with MEM. To each well was added 100 microliters of MEM and 10 microliters of WST-1 cell viability reagent (Roche, Mannheim, Germany) and the plate was placed in a $CO_2$ incubator at 37° C. for 90 minutes. The UV absorbance of the samples were recorded at 450 nm subtracting the absorbance at 650 nm in a Molecular Devices Thermomax plate reader The results of the assay are shown in FIG. 2. The increased number of cells adherent to laminin with increasing concentrations of galectin-3 is clearly revealed. Similarly the lack of significant effect of increasing concentrations of N-terminally truncated galectin-3 is also revealed and is similar to the previously reported data (27). Interestingly, adding the N-terminally truncated galectin-3 blocked the increase in cellular adhesion to laminin mediated by galectin-3. The data clearly show the directly competitive effect of the N-terminally truncated protein on the cellular adhesion that is promoted by intact galectin-3, and supports the mechanism proposed in FIG. 1.

Immunization of Four Chickens with Purified, N-terminally Truncated Galectin-3 and Purification of Polyclonal 1g from Chicken Eggs Two chickens were immunized with purified N-terminally truncated galectin-3 and the polyclonal Ig was purified. The Ig should bind to both galectin-3 and N-terminally truncated galectin-3. When tested, the chicken polyclonal anti-N-terminally truncated galectin-3 was of very low affinity as determined by repeated nitrocellulose dot blots of galectin-3 and N-terminally truncated galectin-3 following lactose elution of each protein from a lactosyl-Sepharose column. The presence of galectin-3 and N-terminally truncated galectin-3 protein in specific fractions from the column was confirmed by the measurement of UV absorbance at 280 nm. Detection of anti-galectin-3 antibody (rat IgG) binding to galectin-3 was used as a positive control on a separate dot blot using anti-rat IgG labeled with alkaline phosphatase (AP). For the chicken polyclonal anti-N-terminally truncated galectin-3 antibody, an anti-chicken Ig antibody (Zymed, South San Francisco) labeled with biotin was used followed by AP-conjugated streptavidin and AP substrate. The results of these studies provided no evidence that immunization of chickens would produce a high affinity antibody specific for N-terminally truncated galectin-3. Therefore, an alternative strategy of generating $^{35}S$-labeled N-terminally truncated galectin-3 was used.

Pharmacokinetic Analysis & Determination of Maximum Tolerated Dose

A dose determination study was carried out in non-tumor bearing female athymic nude mice in order to establish the MTD of N-terminally truncated galectin-3 using a single bolus dose. The dose finding study comprised four dose groups with each group consisting of five mice. The subcutaneous doses administered were 1 mg/kg, 5 mg/kg, 25 mg/kg, and 125 mg/kg. In addition, a vehicle treated control group consisting of five mice was evaluated. No overt abnormal signs were observed within 48 hours of injection. Animals were observed for a total of five days after injection at which time body weight and viability were determined.

The mean body weights for each group were statistically identical (p>0.10; t-test) at five days indicating that all doses of N-terminally truncated galectin-3 did not effect the normal physiological growth of the mice. From these results it was concluded that N-terminally truncated galectin-3 can be injected into nude mice at a dose as high as 125 mg/kg without overt adverse effects.

Perform Pharmacokinetic Analysis Using Standard Methodology.

Figure 5:
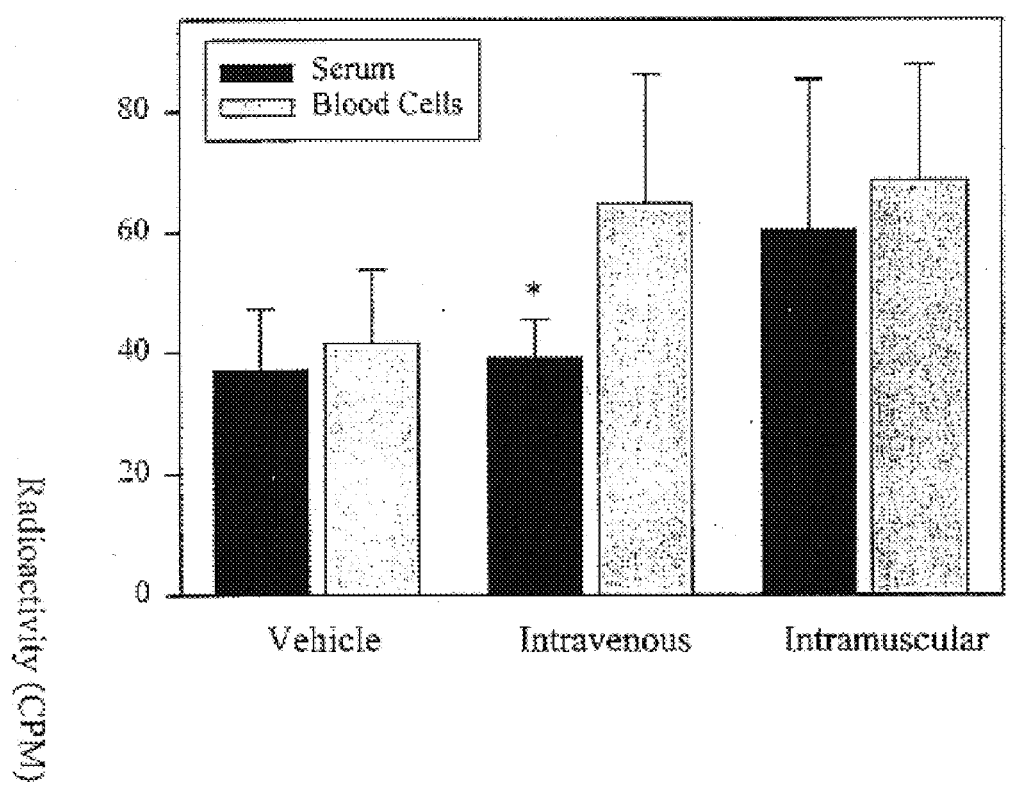
FIG. 5 is a pharmacokinetic analysis of N-terminally truncated galectin-3 at eight hour time points showing the radioactivity based upon either the intravenous or intramuscular administration of N-terminally truncated galectin-3 at an eight hour time frame.

Analyses of the pharmacokinetic and biodistribution characteristics of N-terminally truncated galectin-3 were determined for intravenous and intramuscular routes of administration of N-terminally truncated galectin-3 into nude mice as shown in FIG. 5. Groups of five mice (approximately 0.03 kg/mouse) were each injected with 150 µg/mouse (1 mg per ml; 5 mg/kg=dose) of a mixture of $^{35}$S-labeled N-terminally truncated galectin-3 and unlabeled N-terminally truncated galectin-3 in a weight ratio of 1:9 (labeled:unlabeled). For the intramuscular route, the animals were sacrificed and blood samples were obtained by terminal cardiac puncture at four time points: 2 hours, 4 hours, 8 hours, and 12 hours after injection. In addition, blood samples were obtained from one control group of five animals 1 hour after injection of vehicle only (1 mg/ml lactose in PBS). Serum samples from 200 µl of blood were analyzed for radioactivity in triplicate. For a direct comparison of the pharmacokinetic characteristics of intravenous versus intramuscular administration of N-terminally truncated galectin-3, two groups of five mice each were injected with the mixture of $^{35}$S-labeled N-terminally truncated galectin-3 and unlabeled N-terminally truncated galectin-3 either intravenously or intramuscularly. At eight hours post-injection serum and blood cell samples from 200 µl of blood were analyzed for radioactivity in triplicate. In addition, the organ biodistribution of N-terminally truncated galectin-3 was determined in mice injected subcutaneously and intravenously with the mixture of $^{35}$S-labeled N-terminally truncated galectin-3 and unlabeled N-terminally truncated galectin-3. At eight hours post-injection, the heart, lungs, liver, kidneys, and spleen were removed and the amount of associated radioactivity was measured.

During the distribution phase after an intravenous dose, changes in the concentration of drug are primarily due to movement of drug within the body. The distribution phase primarily determines the early rapid decline in plasma concentration of a drug after an intravenous dose. With time, equilibrium is reached in the distribution of the drug between the plasma and the tissues, and changes in plasma reflect proportional changes in all the other tissues. During the elimination phase, after the rapid decline of the distribution phase, the decline in plasma concentration is due only to elimination of the drug from the body and is characterized by the *elimination half-life* (T½) and the *apparent volume of distribution* (V) (47, 48). The elimination half-life is the time it takes for the concentration of the drug in the plasma (and body) to be reduced by one-half. The apparent volume of distribution is the apparent volume of distribution of the drug in the body at equilibrium. The volume of distribution is equal to the amount of drug in the body at $T_0$ divided by the plasma drug concentration at $T_0$.

In a first-order elimination process the half-life is independent of the concentration of the drug in the body and the following equations apply.

T½=0.693 (where k is the elimination rate constant)   Equation 1.

$$k = \frac{2.303}{Time(2) - Time(1)} \times \log\frac{conc_{Time(1)}}{conc_{Time(2)}}$$   Equation 2.

Figure 4:
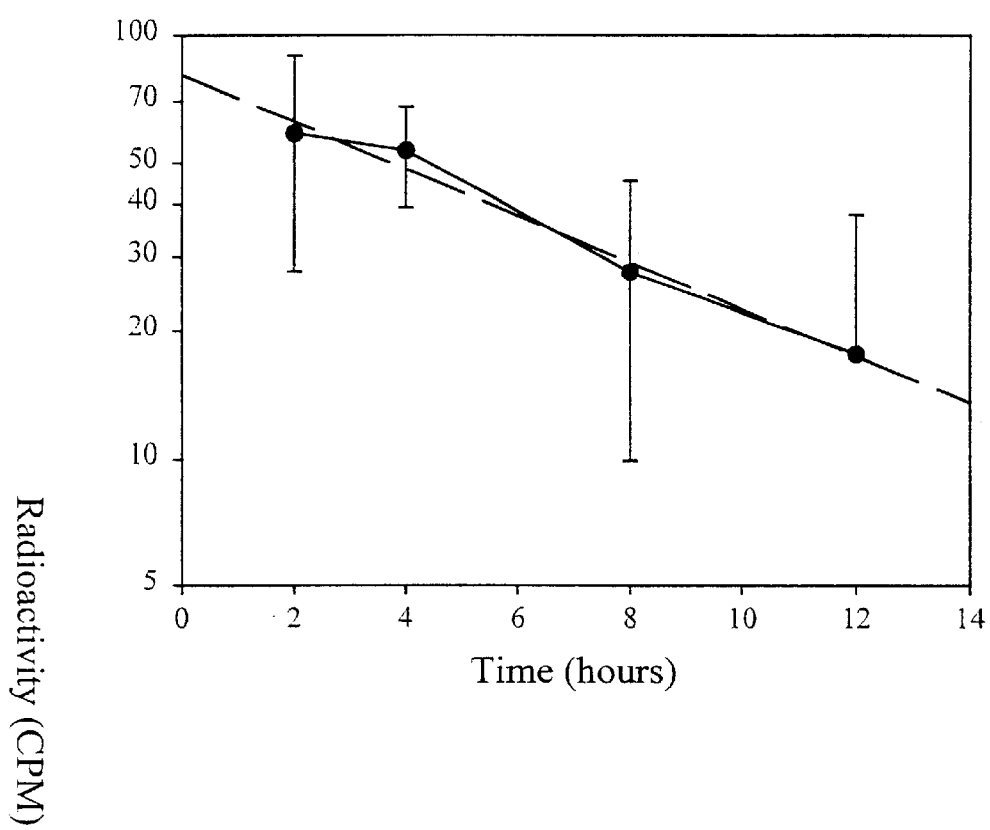
FIG. 4 is a graph showing the intramuscular pharmacokinetic analysis of N-terminally truncated galectin-3 based on the radioactivity versus time.

Calculation of the volume of distribution requires that distribution equilibrium be achieved between the drug in the tissues and the plasma. After administration, the amount of the drug in the body is equal to the dose but the distribution equilibrium has not yet been achieved. To estimate the plasma concentration that would have resulted if the drug immediately distributed into its final volume of distribution, use is made of the linear decline during the elimination phase in the semilogarithmic plot. The pharmacokinetic analysis of the intramuscular administration of N-terminally truncated galectin-3 is shown in FIG. 4. The serum elimination half-life was calculated by regression analysis of the linear portion of the curve between 2 and 12 hours as described above. Thus, for the intramuscular administration of N-terminally truncated galectin-3, k=0.0824 h$^{-1}$ and T½=4.56 h.

The eight hours distribution of N-terminally truncated galectin-3 into serum versus blood cell compartments for N-terminally truncated galectin-3 administered intravenously and intramuscularly were compared. As shown in FIG. 4, both routes of administration resulted in the distribution of N-terminally truncated galectin-3 into serum and blood cells. For intravenous administration, the quantity of N-terminally truncated galectin-3 associated with blood cells was greater than that in serum (p=0.03; t-test). For intramuscular, there was not a statistically significant difference in the amount of N-terminally truncated galectin-3 localized to either compartment. These findings indicate that a portion of the administered N-terminally truncated galectin-3 is associated with blood cells and can serve as a reservoir for slow release in serum.

Figure 6:
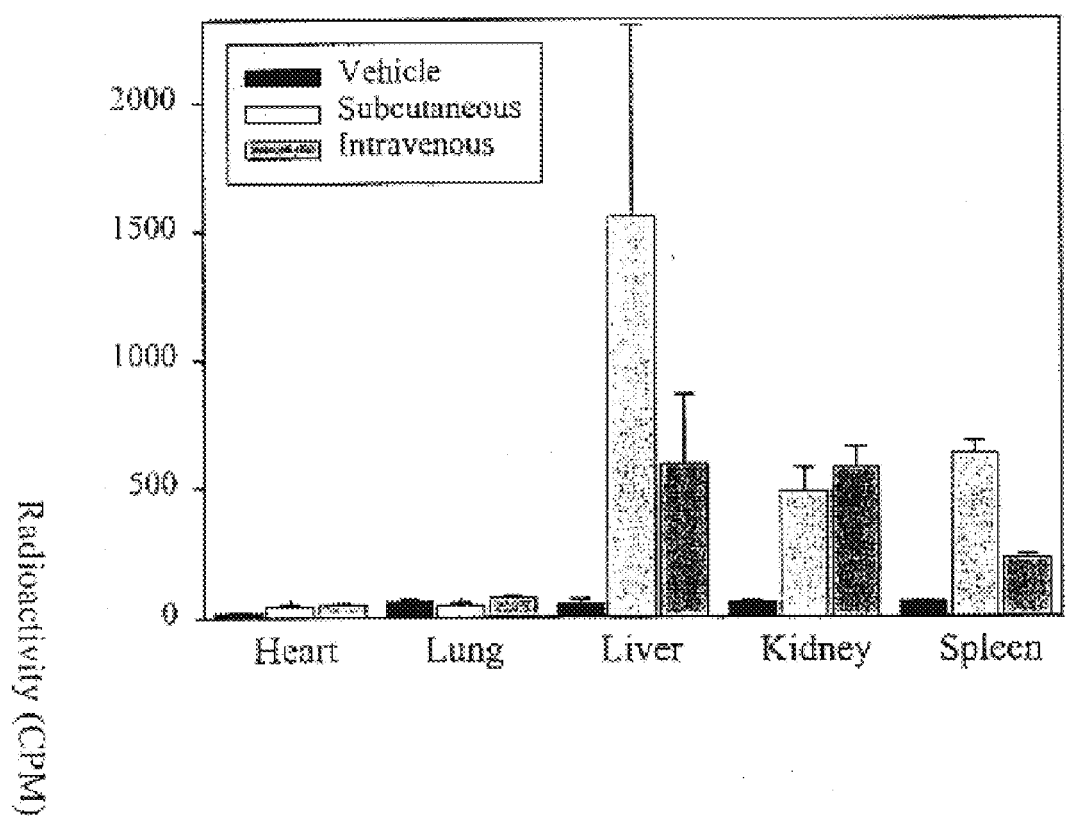
FIG. 6 is a bar graph showing the biodistribution of N-terminally truncated galectin-3 in the heart, lung, liver, kidney, and spleen at eight hour time point.

The organ biodistribution of N-terminally truncated galectin-3 was also investigated. Two groups of five mice were injected either subcutaneously or intravenously with the mixture of $^{35}$S-labeled N-terminally truncated galectin-3 and unlabeled N-terminally truncated galectin-3. A third group of five mice was injected intravenously with the lactose in PBS vehicle. At eight hours post-injection, the heart, lungs, liver, kidneys, and spleen were removed and the amount of associated radioactivity was measured. As shown in FIG. 6, the liver, kidney, and spleen were sources of N-terminally truncated galectin-3-associated radioactivity above the background vehicle level, whereas neither the heart nor lungs localized any N-terminally truncated galectin-3. These data suggest that in addition to serum and blood cells, certain organs can localize N-terminally truncated galectin-3 and possibly serve as reservoirs for eventual systemic release. Alternatively, these organs can function in the ultimate removal of N-terminally truncated galectin-3 from circulation.

Comparison in the MetaMouse$_R$ Model of Metastatic Breast Cancer of the Efficacy of Treatment with N-terminally Truncated Galectin-3 to Control Animals (Vehicle Only)

Female athymic CD-1 nude mice between four and five weeks of age were used in the study. The animals were bred and maintained in a HEPA-filtered environment with cages, food and bedding sterilized by autoclaving. The breeding pairs were obtained from the Charles River Laboratories (Wilmington, Mass.). The animal diets were obtained from Harlan Teklad (Madison, Wis.). Ampicillin (Sigma) at a concentration of 5% (v/v) was added to the autoclaved drinking water.

Breast cancer cell line MDA-MB435, that expresses galectin-3 (49), was transfected with a plasmid expressing green fluorescent protein as previously described (50), and cells were injected into the subcutis of nude mice to form solid tumors. Test animals for the study were transplanted by surgical orthotopic implantation using fragments harvested from the subcutaneously growing tumors. The animals were anesthetized with isoflurane and the surgical area was sterilized using iodine solution and alcohol. An incision approximately 0.5 cm long was made on the second right mammary gland. The gland was then pulled out and two fragments of 1 mm$^3$ of MDA-MB435-GFP tumor tissue were sutured onto the gland with a sterile nylon 8-0 surgical suture. The skin incision was closed with a sterile silk 6-0 surgical suture. All surgical and animal manipulations and procedures were conducted under HEPA-filtered laminar flow hoods.

Extra numbers of mice were transplanted to compensate for possible postsurgical losses and tumor non-takes. The orthotopically-transplanted animals used for the study were selected to establish groups of similar mean tumor size and body weight. Groups for each of the cohort conditions were randomly chosen. The cohort study was grouped as shown in Table 1 for a total of 45 mice. In addition, the production of 50 mg of galectin-3 allowed the testing of five mice with the intact protein. Administration of the treatments was begun when tumors reached palpable sizes. Based on the calculated elimination half-life of N-terminally truncated galectin-3 administered intramuscularly, the dosing schedule for the vehicle control and N-terminally truncated galectin-3 groups was twice a day intramuscular injections with an approximately 6–8 hour interval for 90 days. The dosing for galectin-3 was once a day intramuscular injections. Both N-terminally truncated galectin-3 and galectin-3 were injected as solutions of concentration 1 mg/ml in PBS containing 1 mg/ml lactose. The vehicle control was PBS containing 1 mg/ml lactose.

TABLE 1

Efficacy Test Study Design

| Group | Dose | Dosing Schedule | Number of Mice |
|---|---|---|---|
| Vehicle Control | 125 μl/dose | im, bid × 90 days | 20 |
| N-terminally truncated galectin-3 | 125 μg/dose | im, bid × 90 days | 20 |
| Galectin-3 | 110 μg/dose | im, qd × 90 days | 5 |

Figure 7:
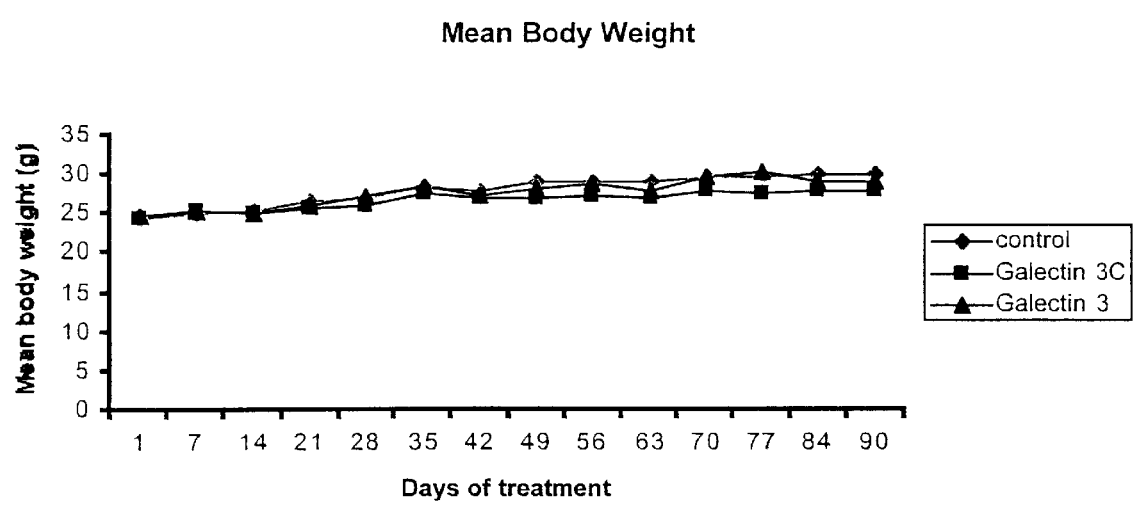
FIG. 7 is a graph showing the mean body weight of a test animal in the control, the N-terminally truncated galectin-3 study, and the galectin-3 study.

Data Collection and Results:

Body weight and animal survival—Animal weight was determined by an electronic balance once a week during the course of the efficacy test. FIG. 7 shows the mean body weights of the mice over time in each of the three treatment groups. The mean body weight of the mice in the control group at day 90 was 30.4±2.89 g, whereas that of the N-terminally truncated galectin-3 treatment group was 28.6±1.91 g. This represents a statistically significant difference in the body weights between the two groups (p=0.026; t-test). The likely explanation for this finding is that the control group had tumors that weighed more than the tumors in the N-terminally truncated galectin-3 group as described below (tumor weight: control mean 2.34 g vs. treated mean 1.25 g). When the difference in tumor weight is factored into the analysis, the difference in mean body weights between the two groups is not statistically significant. In addition, the difference in body weights between the control group and the galectin-3 treated group was not statistically significant.

All animals in all three groups survived the 90 days course of treatment. Thus, no overt toxicity was observed for treatment of mice with either N-terminally truncated galectin-3 or galectin-3 for a period of 90 days.

Figure 8:
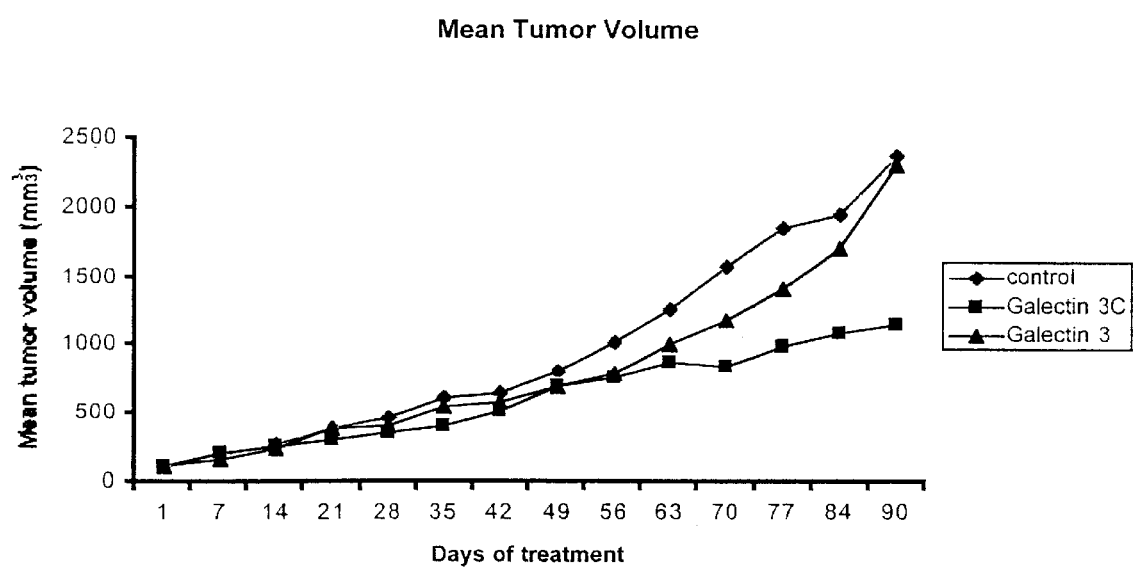
FIG. 8 is a graph showing the mean tumor volume versus the days of treatment with either the control, N-terminally truncated galectin-3 or galectin-3.
Figure 10A:
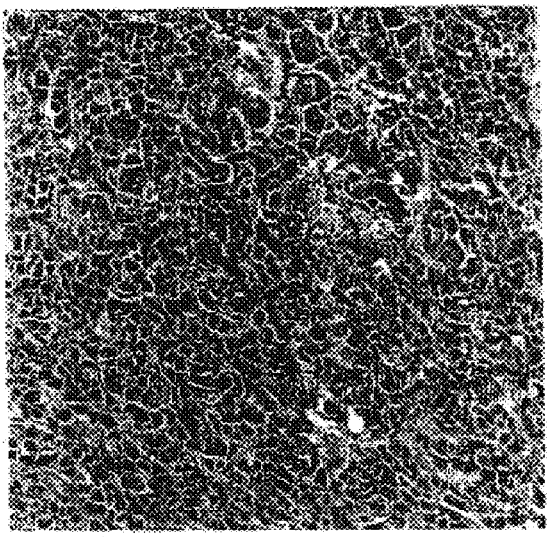
FIGS. 10 A–D are photographs showing a representative histopathology of primary tumor and lymph node, liver and lung metastasis in mice treated with the control.
Figure 10B:
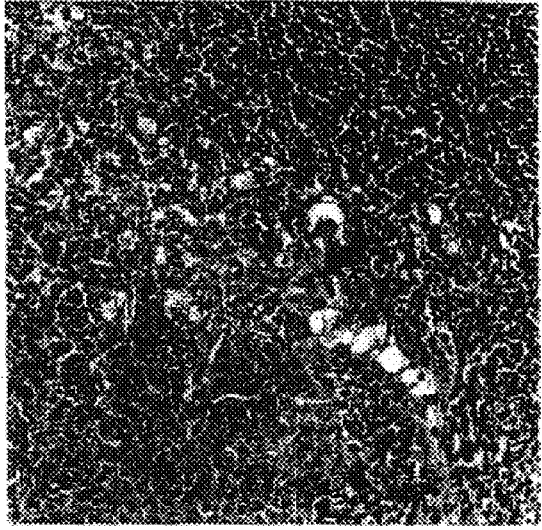
Figure 10C:
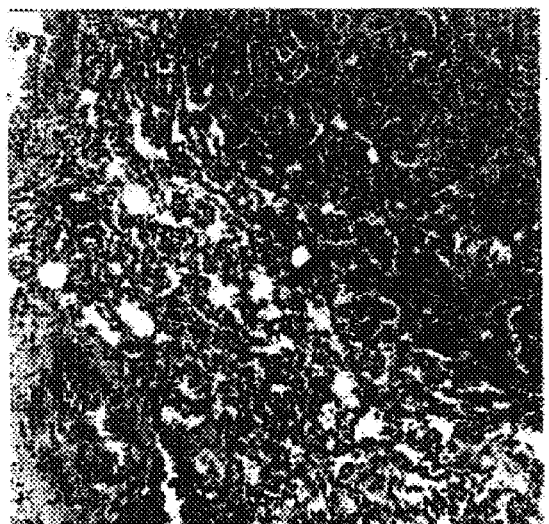
Figure 10D:
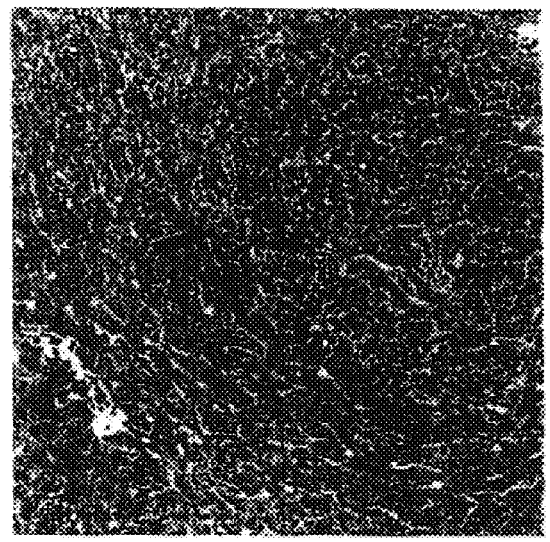
Figure 11A:
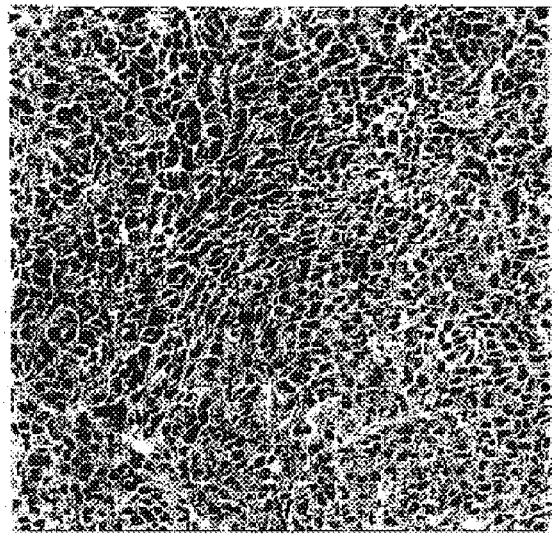
FIGS. 11 A–D are photographs showing a representative histopathology of primary tumor and lymph node, lung and liver metastasis in mice treated with the control.
Figure 11B:
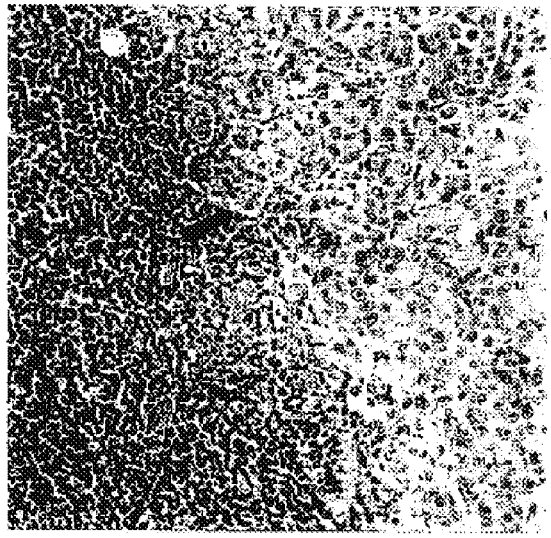
Figure 11C:
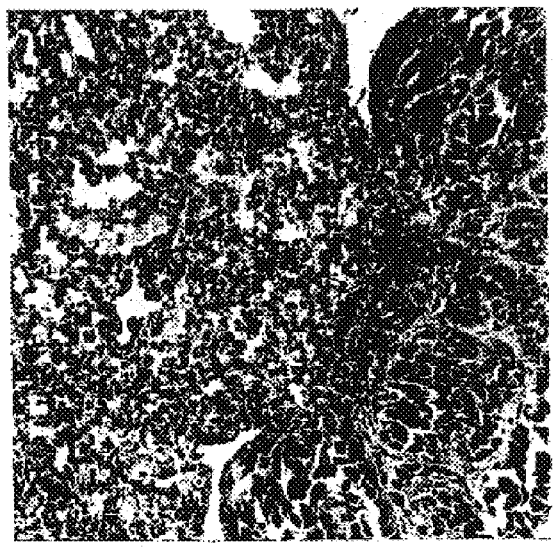
Figure 11D:
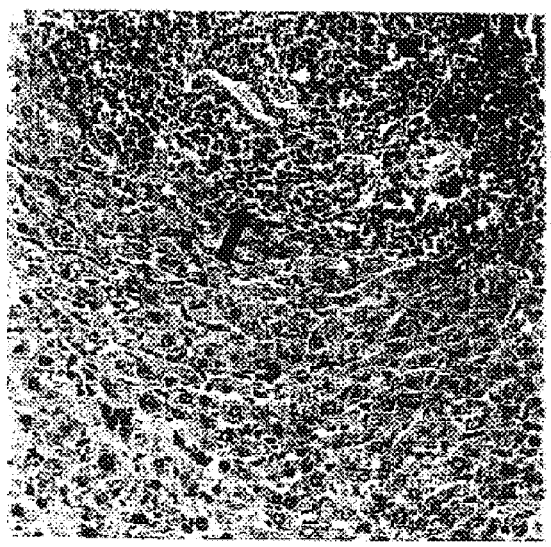
Figure 14A:
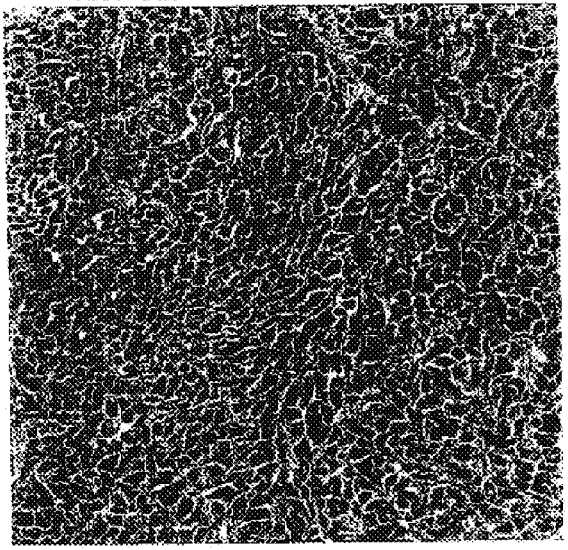
FIGS. 14 A–C are photographs showing a representative histopathology of primary tumor, lymph node, and lung metastasis in mice treated with galectin-3.
Figure 14B:
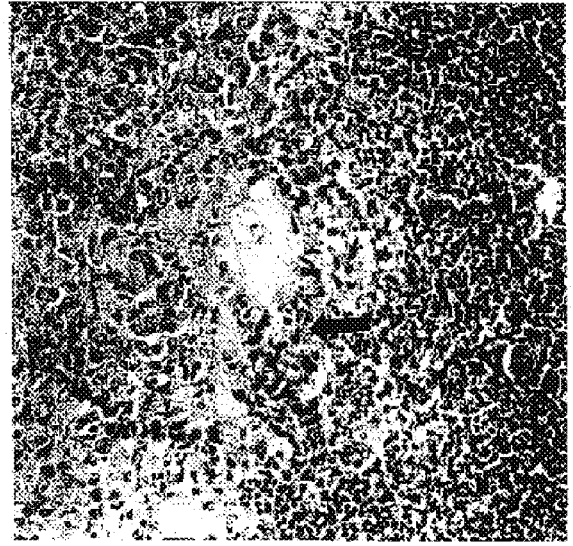
Figure 14C:
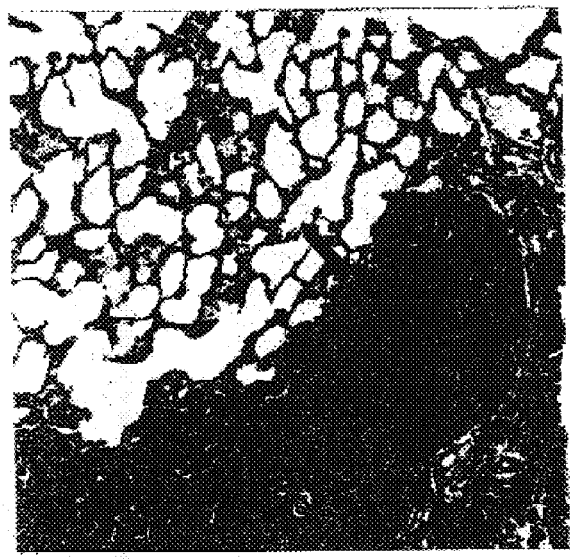

Primary tumor volume and weight—The primary tumors were measured by a pair of calipers once a week after initiation of treatment through the end of the study. The mean tumor volume over time for each treatment group is shown in FIG. 8. Table 2 shows a comparison of the mean tumor volumes of the mice in each group at the end of the treatment regime. The mean tumor volume measured in the mice treated with N-terminally truncated galectin-3 was significantly less than that in the control mice (p=0.003), whereas the mean tumor volume in mice treated with galectin-3 was similar to that in the control mice (p=0.865). Using a whole-body optical imaging system, the growth of the GFP-expressing tumors was also visualized in real time. FIG. 9 shows a 90-day efficacy test of N-terminally truncated galectin-3. Tumor fragments of breast cancer cell line MDA-MB-435 expressing green fluorescent protein were orthotopically implanted into the breast pad of nude mice. Real time, quantitative measurement of tumor growth, metastases, and micrometastases were performed using whole-body optical imaging. The images are representative of the external images of the development of the breast tumor.

Upon autopsy, all visible primary tumors were removed and weighed using an electronic balance. Table 3 shows a comparison of the mean tumor weights at autopsy of mice in each treatment group. The mean tumor weight in the mice treated with N-terminally truncated galectin-3 was significantly less than that in the control mice (p=0.007), whereas the mean tumor volume in mice treated with galectin-3 was similar to that in the control mice (p=0.634).

TABLE 2

Mean tumor volumes at autopsy*

| Group | Number of Mice | Mean primary tumor volume (mm$^3$) ± SD | P value** |
|---|---|---|---|
| Vehicle Control | 20 | 2368.4 ± 1732.7 | — |
| N-terminally truncated galectin-3 | 20 | 1149.2 ± 1679.7 | 0.003 |
| Galectin-3 | 5 | 2307.1 ± 1718.0 | 0.865 |

*Tumor volume was calculated by the formula $W^2 \times L/2$, where W is the smallest dimension.
**All treated groups compared to vehicle control by the Mann-Whitney U test.

TABLE 3

Mean tumor weights at autopsy

| Group | Number of Mice | Mean primary tumor volume (mm$^3$) ± SD | P value* |
|---|---|---|---|
| Vehicle Control | 20 | 2.34 ± 1.47 | — |
| N-terminally truncated galectin-3 | 20 | 1.25 ± 1.65 | 0.007 |
| Galectin-3 | 5 | 2.30 ± 1.44 | 0.634 |

*All treated groups compared to vehicle control by the Mann-Whitney U test.

Assessment of metastasis: At autopsy, tissue samples from the auxiliary lymph node, the liver and the lungs were collected and processed through standard procedures of hematoxylin and eosin staining for subsequent microscopic examination. Representative histopathology of the primary tumors in each group is shown in FIGS. 10–14. No significant pathological differences within primary tumors were noted among the groups.

Metastasis to the auxiliary lymph node, the lung and the liver was assessed microscopically. Representative histopathology of the metastatic tumors in each group is shown in FIGS. 10–14. Table 4 shows the results of this assessment. Statistical analyses were carried out using the Chi-square/Fisher exact test. Eleven out of twenty mice had auxiliary lymph node metastasis in the control group whereas only four of the twenty mice developed auxiliary lymph node metastasis in the N-terminally truncated galectin-3 group by the end of the study (p<0.05). The incidence of metastases in the liver and the lung between the N-terminally truncated galectin-3 group and the control group was not different. Treatment with galectin-3 did not demonstrate a significant difference in metastatic incidence from the control. Tables 5 and 6 show the metastatic data as a function of tumor volumes categorized as small, medium and large. A comparison of the two Tables reveals that five out of the eight small tumors in the control group had associated metastases while 0 of the 15 small tumors in the N-terminally truncated galectin-3 group had associated metastases. This shows that a reduction in tumor volume by N-terminally truncated galectin-3 results in a decreased incidence of metastases.

TABLE 4

Incidence of metastases in lymph node, lung and liver

| Group | Number of Mice | Lymph Node | P value * | Lung | P value | Liver | P value |
|---|---|---|---|---|---|---|---|
| Vehicle Control | 20 | 11/20 | — | 3/20 | — | 2/20 | — |
| Truncated galectin-3 | 20 | 4/20 | 0.022 | 4/20 | 1.0 | 0/20 | 0.487 |
| Galectin-3 | 5 | 1/5 | 0.322 | 1/5 | 1.0 | 0/5 | 1.0 |

*All treated groups compared to vehicle control by the Chi-square/Fisher exact test.

TABLE 5

Number of metastases in control group as a function of tumor volume

| Metastatic assessment | Small tumors (0–1500 mm³) | Medium tumors (1501–2999 mm³) | Large tumors (>2999 mm³) |
|---|---|---|---|
| metastases | 5 (LN only) | 2 (LN only) | 4* |
| no metastases | 3 | 5 | 1 |

*All 4 mice had lymph node metastases; 2 of those had liver and lung metastases, and 1 of those had lung metastases

TABLE 6

Number of metastases in N-terminally truncated galectin-3 group as a function of tumor volume

| Metastatic assessment | Small tumors (0–1500 mm³) | Medium tumors (1501–2999 mm³) | Large tumors (>2999 mm³) |
|---|---|---|---|
| metastases | 0 | 2 (2 lung; 0 liver)* | 2 (2 lung; 0 liver)* |
| no metastases | 15 | 1 | 0 |

*Both mice had lymph node and lung but not liver metastases

In treated animals the number of primary tumors that metastasized was less than controls by a factor of 2.75 (p=0.022), and the mean primary tumor weights of the treated were approximately 2-fold less by the end of the 90-day study (p=0.007).

Statistical methods used in efficacy evaluation (51): Animal body weight comparisons were performed by Student's t-test. The primary tumor volume and weight were evaluated by the Mann-Whitney U test. The incidence of metastasis in the lymph node, lung and the liver were evaluated by the Chi-square/Fisher-exact test. All tests were two-sided with $\alpha=0.05$.

In addition to the statistical data analyses of the efficacy data described above, an analysis of tumor volume growth over time was performed using a repeated measures statistical model for log tumor volume, with cage in random statement. Specifically, this was a SAS Proc Mixed analysis to fit a linear mixed model-with random effects for cage and mouse slope and intercept. The fitted model was quadratic in treatment day. The model was applied to the vehicle control and N-terminally truncated galectin-3 treatment data for tumor volume which showed a significant difference at day 90 when tested with the Mann-Whitney U test. The model allowed us to sensitize the analysis by factoring out non-treatment parameters such as cage and mouse variation, tumor volume trajectory differences within a group, and residual unexplained variation.

Figure 15:
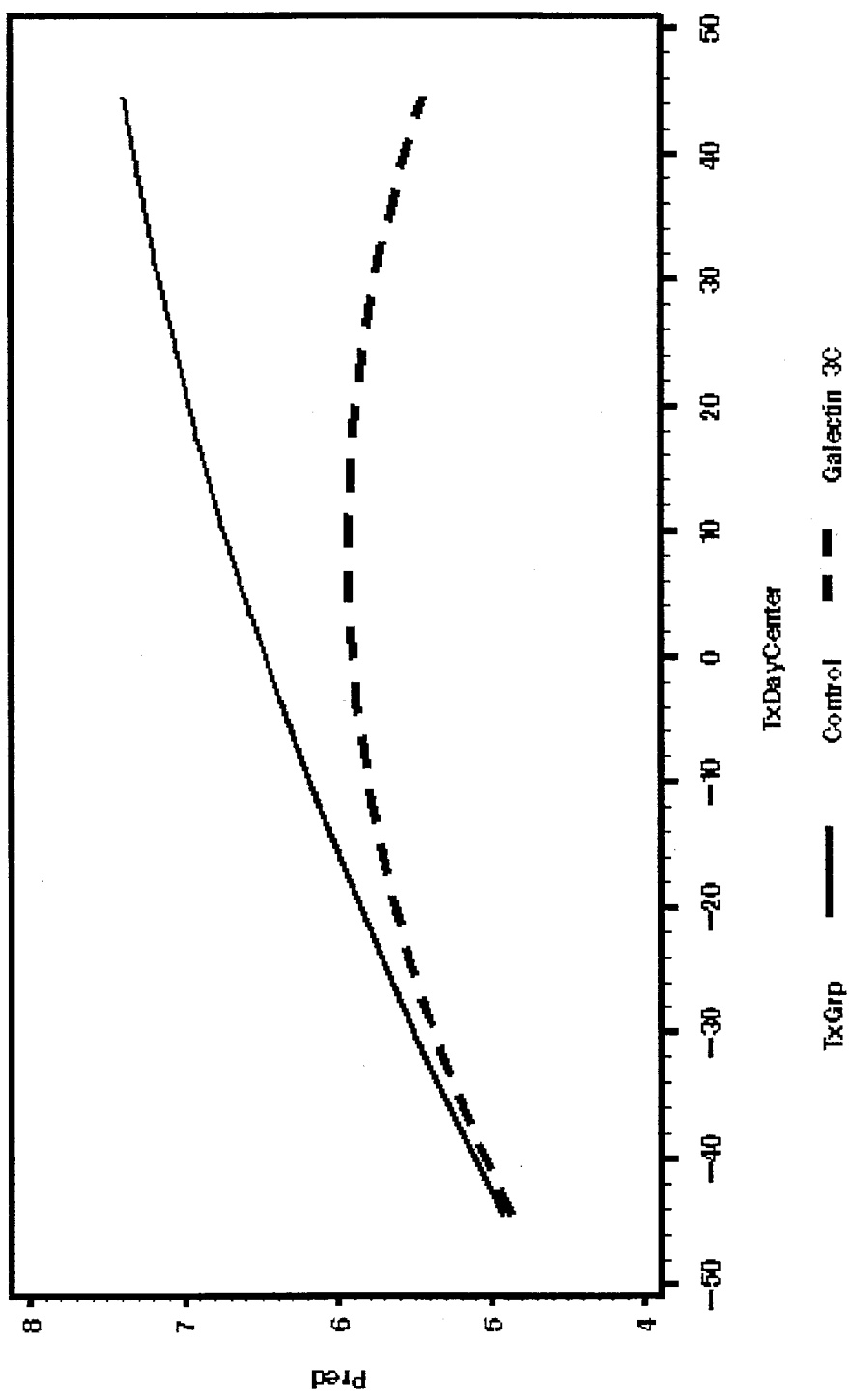
FIG. 15 is a graph showing a repeated measures model for Ln Tumor Volume.

As shown in FIG. 15, the mean tumor volume in the group of mice treated with N-terminally truncated galectin-3 is statistically significantly less than that in the vehicle control group during more than 50% of the treatment period. At day 45 of treatment, which is labeled as TxDayCenter 0 on the x-axis, the slope of the tumor volume curve for the N-terminally truncated galectin-3 group is significantly different than that of the vehicle control group (p=0.045; SAS type 3 F test). Following day 45, treatment with N-terminally truncated galectin-3 resulted in increased differences between the slopes and trajectories of the two lines representing the mean tumor volumes of the two groups of mice. This model strongly supports the conclusion that N-terminally truncated galectin-3 was efficacious in reducing the number of metastases and as well as tumor growth over time in the orthotopic implantation mouse model of breast cancer.

Conclusions

The maximum tolerated dose of N-terminally truncated galectin-3 in nude mice at five days was determined to be greater than 125 mg/kg without overt adverse effects. This suggested that the safety threshold for the use of N-terminally truncated galectin-3 in vivo is high. The pharmacokinetic analysis of the intramuscular administration of $^{35}$S-labeled N-terminally truncated galectin-3 into nude mice indicated an elimination half-life of N-terminally truncated galectin-3 of 4.56 hours. Organ biodistribution analyses showed that N-terminally truncated galectin-3 localized to the liver, kidney, and spleen but not to the heart or lungs.

Based on the pharmacokinetic and maximum tolerated dose data and the amount of N-terminally truncated galectin-3 that was produced, mice were treated twice daily with N-terminally truncated galectin-3 for 90 days and the results were compared with the treatment efficacy with mice treated with vehicle only. At the end of the treatment regime, it was found that the mean tumor volume and mean tumor weight were statistically significantly less in the group of mice treated with N-terminally truncated galectin-3 compared with the group of mice treated with the vehicle control. A repeated measures statistical model for tumor growth over time showed that the mean tumor volume was statistically significantly less by day 45 of the 90 day treatment regime in the group of mice treated with N-terminally truncated galectin-3 compared with the group of mice treated with the vehicle control. In addition, there were statistically significantly fewer numbers of mice which had lymph node metastases in the group of mice treated with N-terminally truncated galectin-3 compared with the vehicle control group of mice.

The hypothesis that was tested was that therapy with recombinant N-terminally truncated galectin-3 is efficacious for inhibition of tumor invasion and metastasis in breast cancer. Taken together, the data generated in this study strongly support this hypothesis. It was found that N-terminally truncated galectin-3 was efficacious in reducing breast cancer metastases in the orthotopic implantation mouse model of breast cancer. Importantly, it was found that N-terminally truncated galectin-3 also reduced tumor volume and tumor weight in the primary tumors. While the mechanisms of action of extracellular N-terminally truncated galectin-3 were not studied, the mechanism is likely to be at least partly due to: 1) decreased homotypic aggregation and adhesion to extracellular matrices human endothelial cells; 2) decreased chemotaxis (galectin-3 itself is a chemotactic factor) (52); or 3) anoikis (apoptosis induced by loss of cell anchorage) (42).

The development of a system for detection of N-terminally truncated galectin-3 in nude mice using $^{35}$S-labeledN-terminally truncated galectin-3 allowed the accurate determination of the in vivo pharmacokinetics of intramuscularly injected N-terminally truncated galectin-3. The fact that N-terminally truncated galectin-3 exhibited no detectable toxicity and reduced tumor volume, tumor weight, and incidence of metastases in a nude mouse model of breast cancer strongly supports further testing of N-terminally truncated galectin-3 as a potential therapeutic compound for the treatment of breast cancer and other types of cancer.

Breast cancer is the most frequently diagnosed cancer in women in the U.S. other than non-melanoma skin cancer that has a much lower mortality rate. Despite the available treatments breast cancer ranks second as the cause of death from cancer in women primarily due to metastases of the primary tumor to other sites in the body. Metastatic breast cancer has a poor prognosis especially if the tumor is hormone-independent, and is the primary cause of mortality in individuals already affected. Based on its minimal toxicity and proven efficacy, it was concluded that N-terminally truncated galectin-3 is a viable candidate for the treatment of breast and other cancers, and that further testing of N-terminally truncated galectin-3 is warranted.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

References

1. Barondes, S. H., D. N. Cooper, M. A. Gitt, and H. Leffler. 1994. Galectins. Structure and function of a large family of animal lectins. *J Biol Chem*. 269:20807–20810.

2. Barondes, S. H., V. Castronovo, D. N. Cooper, R. D. Cummings, K. Drickamer, T. Feizi, M. A. Gitt, J. Hirabayashi, C. Hughes, K. Kasai, and et al. 1994. Galectins: a family of animal beta-galactoside-binding lectins [letter]. *Cell*. 76:597–598.

3. Raz, A., and R. Lotan. 1981. Lectin-like activities associated with human and murine neoplastic cells. *Cancer Res*. 41:3642–3647.

4. Raz, A., G. Pazerini, and P. Carmi. 1989. Identification of the metastasis-associated, galactoside-binding lectin as a chimeric gene product with homology to an IgE-binding protein. *Cancer Res*. 49:3489–3493.

5. Ochieng, J., D. Platt, L. Tait, V. Hogan, T. Raz, P. Carmi, and A. Raz. 1993. Structure-function relationship of a recombinant human galactoside-binding protein. *Biochemistry*. 32:4455–4460.

6. Gong, H. C., Y. Honjo, P. Nangia-Makker, V. Hogan, N. Mazurak, R. S. Bresalier, and A. Raz. 1999. The NH2 terminus of galectin-3 governs cellular compartmentalization and functions in cancer cells. *Cancer Res*. 59:6239–6245.

7. Mehul, B., S. Bawumia, S. R. Martin, and R. C. Hughes. 1994. Structure of baby hamster kidney carbohydrate-binding protein CBP30, an S-type animal lectin. *J Biol Chem*. 269:18250–18258.

8. Seetharaman, J., A. Kanigsberg, R. Slaaby, H. Leffler, S. H. Barondes, and J. M. Rini. 1998. X-ray crystal structure of the human galectin-3 carbohydrate recognition domain at 2.1-A resolution. *J Biol Chem*. 273:13047–13052.

9. Sparrow, C. P., H. Leffler, and S. H. Barondes. 1987. Multiple soluble beta-galactoside-binding lectins from human lung. *J Biol Chem*. 262:7383–7390.

10. Leffier, H., and S. H. Barondes. 1986. Specificity of binding of three soluble rat lung lectins to substituted and unsubstituted mammalian beta-galactosides. *J Biol Chem*. 261:10119–10126.

11. Leffler, H. 1997. Introduction to galectins. *Trends Glycosci Glycotechnol*. 45:9–19.

12. Perillo, N. L., M. E. Marcus, and L. G. Baum. 1998. Galectins: versatile modulators of cell adhesion, cell proliferation, and cell death. *Journal of Molecular Medicine*. 76:402–412.

13. Kaltner, H., K. S. Lips, R. G. Lippert, F. Sinowatz, and H. J. Gabius. 1997. Quantitation and histochemical localization of galectin-1 and galectin-1-reactive glycoconjugates in fetal development of bovine organs. *Histol Histopathol*. 12:945–960.

14. Rabinovich, G. A. 1999. Galectins: an evolutionarily conserved family of animal lectins with multifunctional properties; a trip from the gene to clinical therapy. *Cell Death Differ*. 6:711–721.

15. Rabinovich, G. A., C. M. Riera, C. A. Landa, and C. E. Sotomayor. 1999. Galectins: a key intersection between glycobiology and immunology. *Braz J Med Biol Res*. 32:383–393.

16. Lotz, M. M., C. W. Andrews, Jr., C. A. Korzelius, E. C. Lee, G. D. Steele, Jr., A. Clarke, and A. M. Mercurio. 1993. Decreased expression of Mac-2 (carbohydrate binding protein 35) and loss of its nuclear localization are associated with the neoplastic progression of colon carcinoma. *Proc Natl Acad Sci U S A*. 90:3466–3470.

17. Wang, L., H. Inohara, K. J. Pienta, and A. Raz. 1995. Galectin-3 is a nuclear matrix protein which binds RNA. *Biochem Biophys Res Commun*. 217:292–303.

18. Gaudin, J. C., B. Mehul, and R. C. Hughes. 2000. Nuclear localisation of wild type and mutant galectin-3 in transfected cells. *Biol Cell*. 92:49–58.

19. Lindstedt, R. 1993. Lectins at Epithelial Surfaces. In Department of Medical Microbiology. University of Lund, Lund, Sweden.

20. Lindstedt, T., G. Apodaca, S. H. Barondes, K. Mostov, and H. Leffler. 1993. Apical secretion nof a cytosolic protein by Madin-Darby canine kidney cells. Evidence for polarized release of an endogenous lectin by a nonclassical secretory pathway. *J Biol Chem*. 268:11750–11757.

21. Menon, R. P., and R. C. Hughes. 1999. Determinants in the N-terminal domains of galectin-3 for secretion by a novel pathway circumventing the endoplasmic reticulum-Golgi complex. *Eur J Biochem*. 264:569–576.

22. Prochiantz, A. 2000. Messenger proteins: homeoproteins, TAT and others. *Curr Opin Cell Biol*. 12:400–406.

23. Massa, S. M., D. N. Cooper, H. Leffler, and S. H. Barondes. 1993. L-29, an endogenous lectin, binds to glycoconjugate ligands with positive cooperativity. *Biochemistry*. 32:260–267.

24. Liu, F. T., D. K. Hsu, R. I. Zuberi, P. N. Hill, A. Shenhav, I. Kuwabara, and S. S. Chen. 1996. Modulation of functional properties of galectin-3 by monoclonal antibodies binding to the non-lectin domains. *Biochemistry*. 35:6073–6079.

25. Hsu, D. K., R. I. Suberi, and F. T. Liu. 1992. Biochemical and biophysical characterization of human recombinant IgE-binding protein, an S-type animal lectin. *J. Biol. Chem*. 267:14167–14174.

26. Yamaoka, A., I. Kuwabara, L. G. Frigeri, and F. T. Liu. 1995. A human lectin, galectin-3 (epsilon bp/Mac-2), stimulates superoxide production by neutrophils. *J Immunol*. 154:3479–3487.

27. Kuwabara, I., and F. T. Liu. 1996. Galectin-3 promotes adhesion of human neutrophils to laminin. *J Immunol*. 156:3939–3944.

28. Itzkowitz, S. H. 1997. Galectins: multipurpose carbohydrate-binding proteins implicated in tumor biology. *Gastroenterology*. 113:2003–2005.

29. Ochieng, J., M. L. Leite-Browning, and P. Warfield. 1998. Regulation of cellular adhesion to extracellular matrix proteins by galectin-3. *Biochem Biophys Res Commun*. 246:788–791.

30. Ochieng, J., P. Warfield, B. Green-Jarvis, and 1. Fentie. 1999. Galectin-3 regulates the adhesive interaction between breast carcinoma cells and elastin. *J Cell Biochem*. 75:505–514.

31. Inohara, H., and A. Raz. 1995. Functional evidence that cell surface galectin-3 mediates homotypic cell adhesion. *Cancer Res*. 55:3267–3271.

32. Raz, A., D. G. Zhu, V. Hogan, N. Shah, T. Raz, R. Karkash, G. Pazerini, and P. Carmi. 1990. Evidence for the role of 34-kDa galactoside-binding lectin in transformation and metastasis. *Int J Cancer*. 46:871–877.

33. Nangia-Makker, P., Y. Honjo, R. Sarvis, S. Akahani, V. Hogan, K. J. Pienta, and A. Raz. 2000. Galectin-3 induces endothelial cell morphogenesis and angiogenesis. *Am J Pathol*. 156:899–909.

34. Bresalier, R. S., N. Mazurek, L. R. Sternberg, J. C. Byrd, C. K. Yunker, P. Nangia-Makker, and A. Raz. 1998. Metastasis of human colon cancer is altered by modifying expression of the beta-galactoside-binding protein galectin 3. *Gastroenterology*. 115:287–296.

35. Le Marer, N., and R. C. Hughes. 1996. Effects of the carbohydrate-binding protein galectin-3 on the invasiveness of human breast carcinoma cells. *J Cell Physiol*. 168:51–58.

36. Nangia-Makker, P., R. Sarvis, D. W. Visscher, J. Bailey-Penrod, A. Raz, and F. H. Sarkar. 1998. Galectin-3 and L1 retrotransposons in human breast carcinomas. *Breast Cancer Res Treat*. 49:171–183.

37. Castronovo, V., F. A. Van Den Brule, P. Jackers, N. Clausse, F. T. Liu, C. Gillet, and M. E. Sobel. 1996. Decreased expression of galectin-3 is associated with progression of human breast cancer. *J Pathol*. 179:43–48.

38. Idikio, H. 1998. Galectin-3 expression in human breast carcinoma: correlation with cancer histologic grade. *Int J Oncol*. 12:1287–1290.

39. Andre, S., S. Kojima, N. Yamazaki, C. Fink, H. Kaltner, K. Kayser, and H. J. Gabius. 1999. Galectins-1 and -3 and their ligands in tumor biology. Non-uniform properties in cell-surface presentation and modulation of adhesion to matrix glycoproteins for various tumor cell lines, in biodistribution of free and liposome-bound galectins and in their expression by breast and colorectal carcinomas with/without metastatic propensity. *J Cancer Res Clin Oncol*. 125:461–474.

40. Yang, R.-Y., D. Hsu, and F.-T. Liu. 1996. Expression of galectin-3 modulates T-cell growth and apoptosis. *Proc Natl Acad Sci USA*. 93:6737–6742.

41. Akahani, S., P. Nangia-Makker, H. Inohara, H. R. Kim, and A. Raz. 1997. Galectin-3: a novel antiapoptotic molecule with a functional BH1 (NWGR) domain of Bcl-2 family. *Cancer Res*. 57:5272–5276.

42. Kim, H. R., H. M. Lin, H. Biliran, and A. Raz. 1999. Cell cycle arrest and inhibition of anoikis by galectin-3 in human breast epithelial cells. *Cancer Res*. 59:4148–4154.

43. Matarrese, P., O. Fusco, N. Tinari, C. Natoli, F. T. Liu, M. L. Semeraro, W. Malorni, and S. Iacobelli. 2000. Galectin-3 overexpression protects from apoptosis by improving cell adhesion properties. *Int J Cancer*. 85:545–554.

44. Matarrese, P., N. Tinari, M. Semeraro, C. Natoli, S. Iacobelli, and W. Malorni. 2000. Galectin-3 overexpression protects from cell damage and death by influencing mitochrondrial homeostatis. *FEBS letters*. 473:311–315.

45. Pienta, K. J., H. Naik, A. Akhtar, K. Yamazaki, T. S. Replogle, J. Lehr, T. L. Donat, L. Tait, V. Hogan, and A. Raz. 1995. Inhibition of spontaneous metastasis in a rat prostate cancer model by oral administration of modified citrus pectin [see comments]. *J Natl Cancer Inst*. 87:348–353.

46. Oda, Y., H. Leffler, Y. Sakakura, K. Kasai, and S. H. Barondes. 1991. Human breast carcinoma cDNA encoding a galactoside-binding lectin homologous to mouse Mac-2 antigen. *Gene*. 99:279–283.

47. Martin, A. N., J. Swarbrick, and A. Cammarata. 1996. Physical Pharmacy. Lea & Febiger, Philadelphia.

48. Rowland, M., and T. N. Tozer. 1995. Clinical Pharmacokinetics. Williams & Wilkins, Baltimore.

49. Glinsky, V. V., M. E. Huflejt, G. V. Glinsky, S. L. Deutscher, and T. P. Quinn. 2000. Effects of Thomsen-Friedenreich antigen-specific peptide P-30 on beta-galactoside-mediated homotypic aggregation and adhesion to the endothelium of MDA-MB-435 human breast carcinoma cells. *Cancer Res*. 60:2584–2588.

50. Yang, M., E. Baranov, P. Jiang, F.-X. Sun, X.-M. Li, S. Hasegawa, M. Bouvet, M. Al-Tuwaijri, T. Chishima, H. Shimada, A. Moossa, S. Penman, and R. Hoffman. 2000. Whole-body optical imaging of green fluorescent protein-expressing tumors and metastases. *Proc Natl Acad Sci USA*. 97:1206–1211.

51. Zar, J. H. 1996. Biostatistical Analysis. Prentice-Hall, Englewood Cliffs, N.J.

52. Sano, H., D. K. Hsu, L. Yu, J. R. Apgar, I. Kuwabara, T. Yamanaka, M. Hirashima, and F. T. Liu. 2000. Human galectin-3 is a novel chemoattractant for monocytes and macrophages. *J Immunol*. 165:2156–2164.

What is claimed is:

1. A composition comprising N-terminally truncated galectin-3 consisting of a sequence as set forth in SEQ ID No.:1 and a pharmaceutically acceptable carrier for treating cancer.

2. The composition according to claim 1, wherein said N-terminally truncated galectin-3 is present in an amount sufficient to reduce metastasis and tumor size.

* * * * *

UNITED STATES PATENT AND TRADEMARK OFFICE
CERTIFICATE OF CORRECTION

PATENT NO. : 6,770,622 B2
DATED : August 3, 2004
INVENTOR(S) : Gary A. Jarvis et al.

It is certified that error appears in the above-identified patent and that said Letters Patent is hereby corrected as shown below:

<u>Column 13,</u>
Lines 21-22, should read:
-- …and cleaved with Clostridium histolyticum collagenase type VII (Sigma) --

Signed and Sealed this

Tenth Day of May, 2005

JON W. DUDAS
*Director of the United States Patent and Trademark Office*

SEQUENCE LISTING

<160> NUMBER OF SEQ ID NOS: 4

<210> SEQ ID NO 1
<211> LENGTH: 143
<212> TYPE: PRT
<213> ORGANISM: homo sapien

<400> SEQUENCE: 1

Gly Ala Pro Ala Gly Pro Leu Ile Val Pro Tyr Asn Leu Pro Leu Pro
1               5                   10                  15

Gly Gly Val Val Pro Arg Met Leu Ile Thr Ile Leu Gly Thr Val Lys
            20                  25                  30

Pro Asn Ala Asn Arg Ile Ala Leu Asp Phe Gln Arg Gly Asn Asp Val
        35                  40                  45

Ala Phe His Phe Asn Pro Arg Phe Asn Glu Asn Asn Arg Arg Val Ile
    50                  55                  60

Val Cys Asn Thr Lys Leu Asp Asn Asn Trp Gly Arg Glu Glu Arg Gln
65                  70                  75                  80

Ser Val Phe Pro Phe Glu Ser Gly Lys Pro Phe Lys Ile Gln Val Leu
                85                  90                  95

Val Glu Pro Asp His Phe Lys Val Ala Val Asn Asp Ala His Leu Leu
            100                 105                 110

Gln Tyr Asn His Arg Val Lys Lys Leu Asn Glu Ile Ser Lys Leu Gly
        115                 120                 125

Ile Ser Gly Asp Ile Asp Leu Thr Ser Ala Ser Tyr Thr Met Ile
    130                 135                 140

<210> SEQ ID NO 2
<211> LENGTH: 250
<212> TYPE: PRT
<213> ORGANISM: homo sapien

<400> SEQUENCE: 2

Met Ala Asp Asn Phe Ser Leu His Asp Ala Leu Ser Gly Ser Gly Asn
1               5                   10                  15

Pro Asn Pro Gln Gly Trp Pro Gly Ala Trp Gly Asn Gln Pro Ala Gly
            20                  25                  30

Ala Gly Gly Tyr Pro Gly Ala Ser Tyr Pro Gly Ala Tyr Pro Gly Gln
        35                  40                  45

Ala Pro Pro Gly Ala Tyr Pro Gly Gln Ala Pro Pro Gly Ala Tyr His
    50                  55                  60

Gly Ala Pro Gly Ala Tyr Pro Gly Ala Pro Ala Pro Gly Val Tyr Pro
65                  70                  75                  80

Gly Pro Pro Ser Gly Pro Gly Ala Tyr Pro Ser Ser Gly Gln Pro Ser
                85                  90                  95

Ala Pro Gly Ala Tyr Pro Ala Thr Gly Pro Tyr Gly Ala Pro Ala Gly
            100                 105                 110

Pro Leu Ile Val Pro Tyr Asn Leu Pro Leu Pro Gly Gly Val Val Pro
        115                 120                 125

Arg Met Leu Ile Thr Ile Leu Gly Thr Val Lys Pro Asn Ala Asn Arg
    130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

```
Leu Asp Asn Asn Trp Gly Arg Glu Glu Arg Gln Ser Val Phe Pro Phe
            180                 185                 190

Glu Ser Gly Lys Pro Phe Lys Ile Gln Val Leu Val Glu Pro Asp His
        195                 200                 205

Phe Lys Val Ala Val Asn Asp Ala His Leu Leu Gln Tyr Asn His Arg
    210                 215                 220

Val Lys Lys Leu Asn Glu Ile Ser Lys Leu Gly Ile Ser Gly Asp Ile
225                 230                 235                 240

Asp Leu Thr Ser Ala Ser Tyr Thr Met Ile
                245                 250

<210> SEQ ID NO 3
<211> LENGTH: 33
<212> TYPE: DNA
<213> ORGANISM: artificial sequence
<220> FEATURE:
<221> NAME/KEY: artificial sequence
<222> LOCATION: (1)..(33)
<223> OTHER INFORMATION: primer

<400> SEQUENCE: 3
gacgacgaca agggcgcccc tgctgggcca ctg                              33

<210> SEQ ID NO 4
<211> LENGTH: 34
<212> TYPE: DNA
<213> ORGANISM: artificial sequence
<220> FEATURE:
<221> NAME/KEY: artificial sequence
<222> LOCATION: (1)..(34)
<223> OTHER INFORMATION: primer

<400> SEQUENCE: 4
gaggagaagc ccggtgcccc tttcagatta tatc                             34
```